(12) United States Patent
Burg et al.

(10) Patent No.: US 11,131,633 B2
(45) Date of Patent: *Sep. 28, 2021

(54) QUANTIFYING COLOR CHANGES OF CHEMICAL TEST PADS INDUCED BY SPECIFIC CONCENTRATIONS OF BIOLOGICAL ANALYTES UNDER DIFFERENT LIGHTING CONDITIONS

(71) Applicant: HEALTHY.IO LTD., Tele Aviv-Jaffa (IL)

(72) Inventors: Bernard Burg, Menlo Park, CA (US); Martin Zizi, Enines (BE); Aaron Alexander Rowe, San Francisco, CA (US); Anthony Smart, Costa Mesa, CA (US); Walter De Brouwer, Los Altos, CA (US)

(73) Assignee: HEALTHY.IO LTD., Tel Aviv-Jaffa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/297,630

(22) Filed: Mar. 9, 2019

(65) Prior Publication Data

US 2019/0310203 A1 Oct. 10, 2019

Related U.S. Application Data

(63) Continuation of application No. 15/055,643, filed on Feb. 29, 2016, now Pat. No. 10,267,743, which is a (Continued)

(51) Int. Cl.
*G01N 21/78* (2006.01)
*G01N 21/79* (2006.01)
(Continued)

(52) U.S. Cl.
CPC ............ *G01N 21/78* (2013.01); *G01N 21/79* (2013.01); *G01N 33/48* (2013.01);
(Continued)

(58) Field of Classification Search
CPC ... G01N 2021/7759; G01N 2021/1765; G01N 2021/8488; G01N 21/77; G01N 21/78;
(Continued)

(56) References Cited

U.S. PATENT DOCUMENTS 5,408,535 A 4/1995 Howard, III et al.
6,285,454 B1 9/2001 Douglas et al.
(Continued)

FOREIGN PATENT DOCUMENTS

DE 102010011838 A1 9/2011
EP 2646809 B1 8/2018
(Continued)

*Primary Examiner* — Maureen Wallenhorst
(74) *Attorney, Agent, or Firm* — Finnegan, Henderson, Farabow, Garrett & Dunner, LLP

(57) ABSTRACT

Color quantification of chemical test pads and titration of analytes can be performed under different lighting conditions. In one embodiment, the lighting condition is estimated under which a digital image is captured and utilized to select a set of reference colors from which the quantified color is compared to determine the titration. In another embodiment, a plurality of comparisons are made with different lighting conditions with the result having the highest confidence level being selected to determine the titration.

18 Claims, 28 Drawing Sheets

Related U.S. Application Data continuation of application No. 14/633,513, filed on Feb. 27, 2015, now Pat. No. 9,285,323, which is a continuation-in-part of application No. 14/419,939, filed as application No. PCT/US2013/035397 on Apr. 5, 2013, now Pat. No. 9,311,520.

(60) Provisional application No. 61/948,356, filed on Mar. 5, 2014, provisional application No. 61/680,842, filed on Aug. 8, 2012.

(51) Int. Cl.
*G01N 33/48* (2006.01)
*G01N 21/77* (2006.01)

(52) U.S. Cl.
CPC ............ *G01N 2021/7759* (2013.01); *G01N 2201/0221* (2013.01); *G01N 2201/12* (2013.01)

(58) Field of Classification Search
CPC ...... G01N 21/79; G01N 21/27; G01N 21/274; G01N 21/8483; G01N 2201/0221; G01N 2201/12; G01N 33/48; G01N 33/49; G01N 33/493; G01N 2035/00108; G01N 35/00029; G01J 3/46; G01J 3/50; G01J 3/02; G01J 3/524; G01J 3/51
USPC .......... 436/63, 164, 169, 172; 422/400–403, 422/420, 82.05, 82.08; 435/29, 288.7; 356/402
See application file for complete search history.

(56) References Cited

U.S. PATENT DOCUMENTS

| | | | |
|---|---|---|---|
| 9,285,323 B2 * | 3/2016 | Burg | G01N 21/78 |
| 9,311,520 B2 * | 4/2016 | Burg | G01N 35/00029 |
| 9,528,941 B2 * | 12/2016 | Burg | G01N 21/78 |
| 9,607,380 B2 * | 3/2017 | Burg | G01N 35/00029 |
| 9,863,811 B2 * | 1/2018 | Burg | G01J 1/4204 |
| 9,903,857 B2 | 2/2018 | Polwart et al. | |
| 10,267,743 B2 * | 4/2019 | Burg | G01N 21/78 |
| 2002/0086435 A1 * | 7/2002 | Fernandez Decastro | G01N 33/526 436/164 |
| 2005/0157304 A1 | 7/2005 | Xiao et al. | |
| 2006/0292040 A1 | 12/2006 | Wickstead et al. | |
| 2010/0254581 A1 * | 10/2010 | Neeser | A61B 5/0077 382/128 |
| 2012/0063652 A1 * | 3/2012 | Chen | G01N 21/274 382/128 |
| 2012/0106811 A1 | 5/2012 | Chen et al. | |
| 2012/0178101 A1 | 7/2012 | Bae et al. | |
| 2012/0282154 A1 | 11/2012 | Slowly et al. | |
| 2014/0242612 A1 | 8/2014 | Wang et al. | |

FOREIGN PATENT DOCUMENTS

| | | |
|---|---|---|
| EP | 3470825 A1 | 4/2019 |
| KR | 1020100008840 A | 1/2010 |
| KR | 1020110024747 A | 3/2011 |
| WO | WO 2007/079843 A2 | 7/2007 |

* cited by examiner

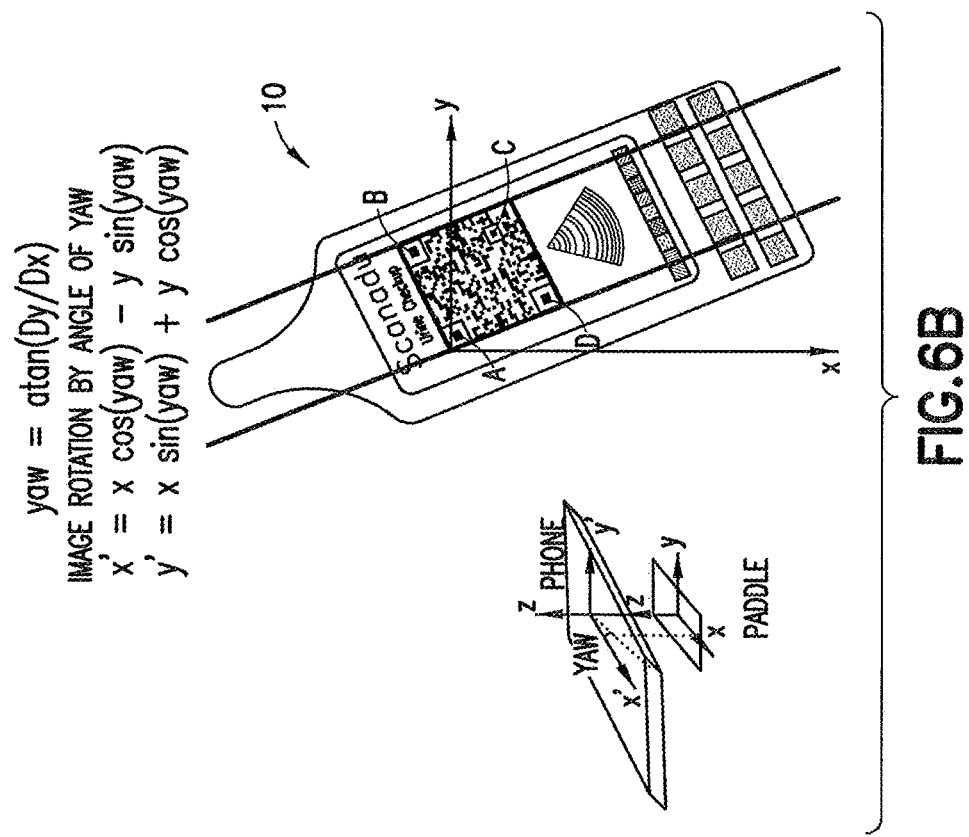
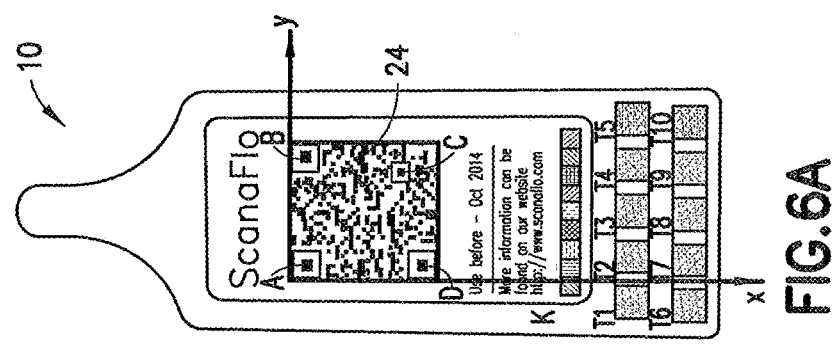
FIG. 6A
FIG. 6B

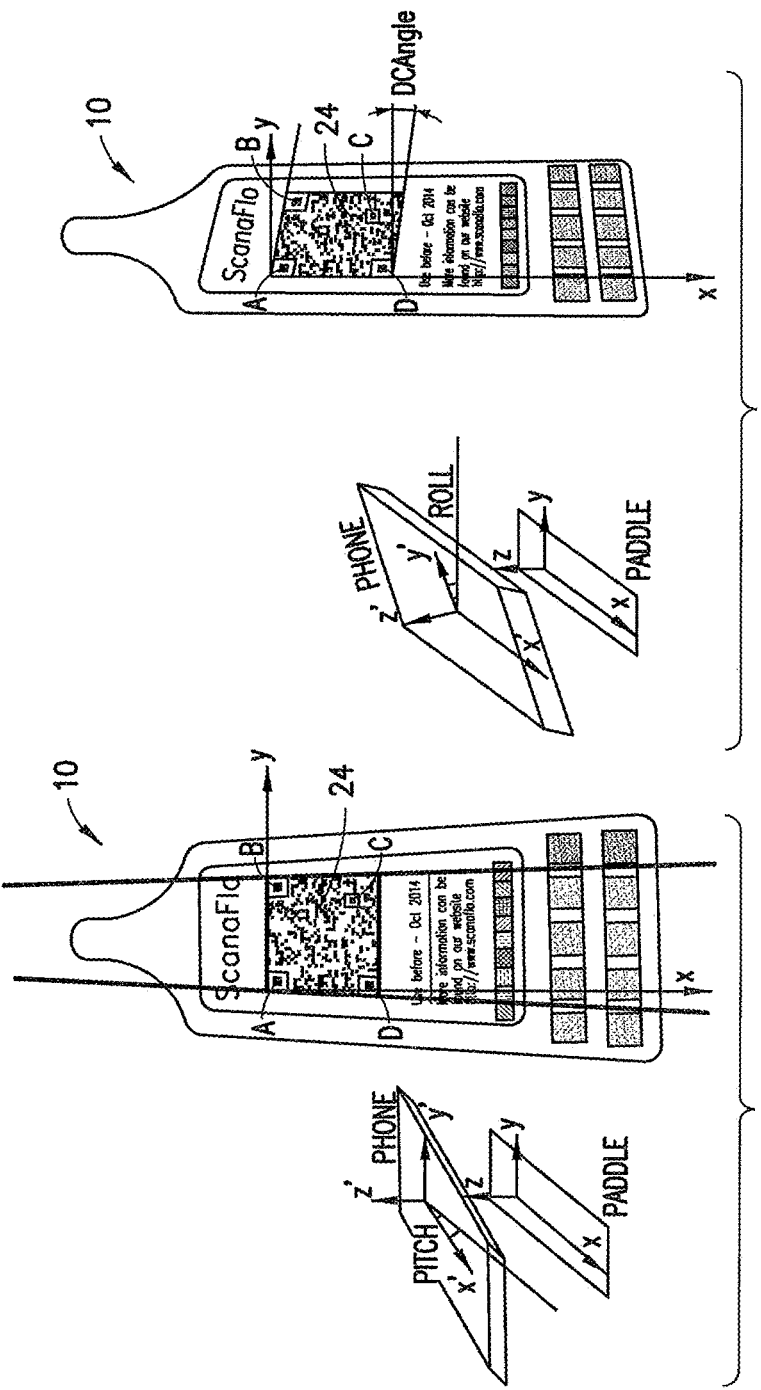

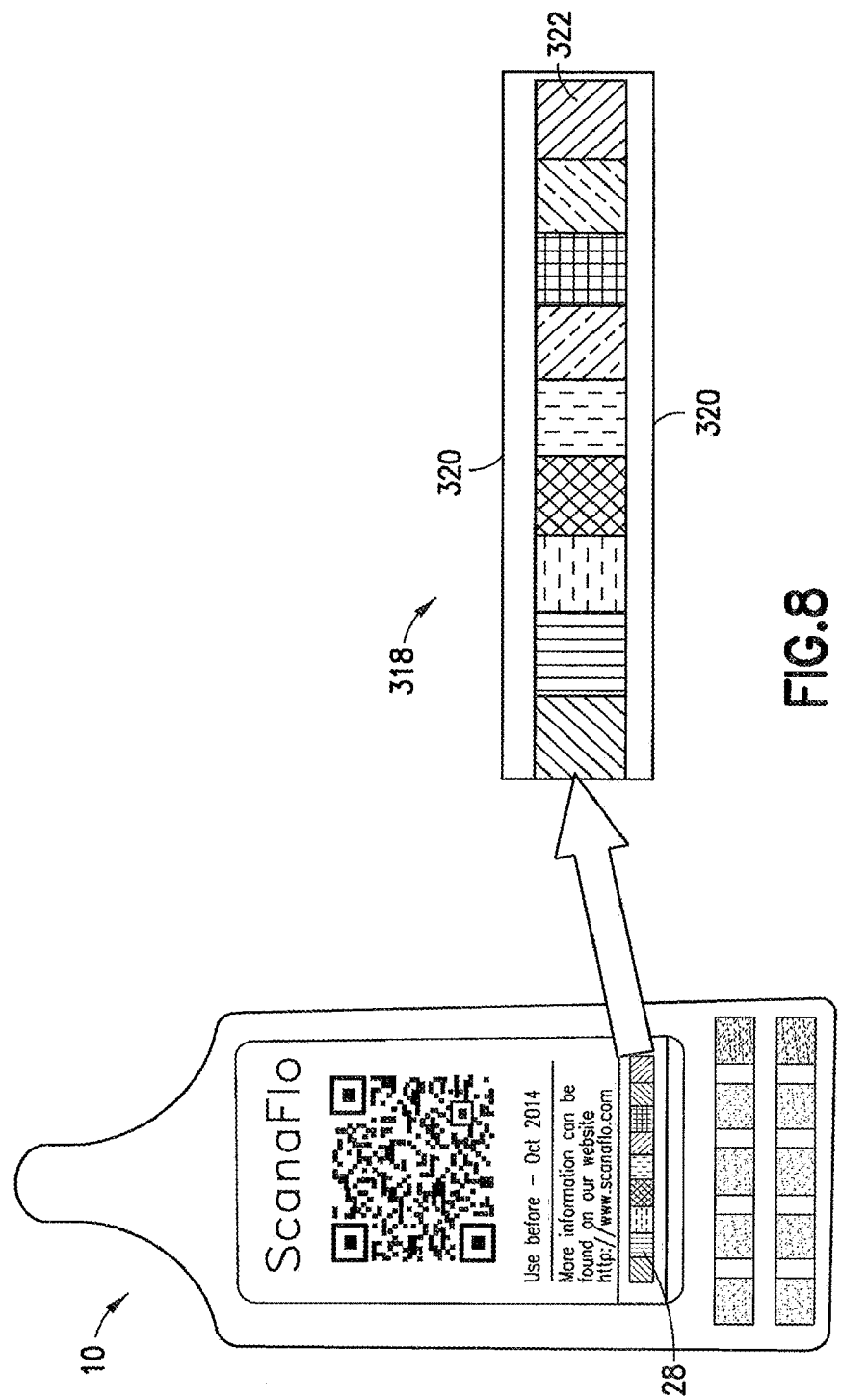

FIG. 14

URINE LEUCOCYTES

Q : [Urine are cloudy ?/unusual smell ?]

| Possible causes | Prompted Questions | Associated readings |
|---|---|---|
| Urinary tract Infection | | |
|   Bladder | [frequent needs to urinate] | [blood, sometimes] [nitrites] |
|   Kidney | [if high fever] | [blood] [nitrites] |
| Inflammation | | |
| Pregnancy | [pregnant] | [Proteins] |
| Sexual activity | [new partner] | |
| | [increase in activity] | |
| Physical damage | | |
|   To Kidney | [antecedents of stones] | [Proteins] [blood] [creatinine] |
| | [known kidney disease] | |
|   To prostate | [known prostatic problems] | [Proteins] [blood] |
| Physical anomaly | [kidney duplication,...] | |
| False positive | [poor sample collection] | |

FIG. 15

URINARY PROTEINS

Q: [Urine foamy?]
[Transient?]
[Permanent? More than 2 readings a few weeks apart]

*If TRANSIENT:*

| Possible causes | Prompted Questions | Associated readings |
|---|---|---|
| High fever | [Fever] | |
| Extreme temperatures | [external temp] [Physical activity] | |
| Sport activities | [Increased physical activity] [Extreme physical activity] | [Blood, Hemoglobin++] |
| Stress ++ | [Stress or unusual event] | |

*If PERMANENT:*

| Possible causes | Prompted Questions | Associated readings |
|---|---|---|
| Urinary tract Infection | | |
| Bladder | [frequent needs to urinate] | [blood, sometimes] [nitrites] [leucocytes] |
| Kidney | [if high fever] | [blood] [nitrites] [leucocytes] |
| High Blood pressure | [BP] | [blood traces, sometimes] |
| Kidney diseases | | |
| Stones | [antecedents of stones] [known kidney disease] | [Proteins] [blood] [creatinine] |
| Consecutive to Systemic (see below) | | |
| Heart problems | [heart condition, …] | |
| Pre-eclampsia | [pregnancy] [high blood pressure] [sudden weight gain/ water retention] | [blood] |
| Diabetes (advanced) | [known?, duration?, insulin or not?] [vascular problems] [difficulty to march] [loss of sensility: hands, feet,…] | [sugar] [blood] [creatinine] |
| Drugs side effects | [intake of antibiotics] [Intake of aminoglycosides (names)] [altered hearing] [recent use of painkiller] [Intake of phenazone derivatives (names)] | [creatinine] |
| Systemic diseases | [known SD] [high blood pressure, sometimes] | [blood, sometimes] [creatinine] [bilirubine] [leucocytes] | ex of SD: Rheumatoid arthritis, Hodgkin lymphoma, multiple myeloma...

QUANTIFYING COLOR CHANGES OF CHEMICAL TEST PADS INDUCED BY SPECIFIC CONCENTRATIONS OF BIOLOGICAL ANALYTES UNDER DIFFERENT LIGHTING CONDITIONS

CROSS REFERENCE TO RELATED APPLICATIONS

This application is a continuation and claims the benefit of United States (U.S.) patent application Ser. No. 15/055,643 entitled QUANTIFYING COLOR CHANGES OF CHEMICAL TEST PADS INDUCED BY SPECIFIC CONCENTRATIONS OF BIOLOGICAL ANALYTES UNDER DIFFERENT LIGHTING CONDITIONS filed Feb. 29, 2016 by inventors Bernard Burg et al., issued as U.S. Pat. No. 10,267,743. U.S. application Ser. No. 15/055,643 is a continuation and claims the benefit of United States (U.S.) patent application Ser. No. 14/633,513 entitled QUANTIFYING COLOR CHANGES OF CHEMICAL TEST PADS INDUCED BY SPECIFIC CONCENTRATIONS OF BIOLOGICAL ANALYTES UNDER DIFFERENT LIGHTING CONDITIONS filed Feb. 27, 2015 by inventors Bernard Burg et al., issued as U.S. Pat. No. 9,285,323. U.S. application Ser. No. 14/633,513 claims the benefit of U.S. Provisional Patent Application No. 61/948,536 entitled APPARATUS FOR DETERMINING ANALYTE CONCENTRATION BY QUANTIFYING AND INTERPRETING COLOR INFORMATION CAPTURED IN A CONTINUOUS OR PERIODIC MANNER filed Mar. 5, 2014 and incorporated herein by reference.

This application further is a continuation in part claiming the benefit of U.S. patent application Ser. No. 14/419,939 entitled METHOD AND APPARATUS FOR PERFORMING AND QUANTIFYING COLOR CHANGES INDUCED BY SPECIFIC CONCENTRATIONS OF BIOLOGICAL ANALYTES IN AN AUTOMATICALLY CALIBRATED ENVIRONMENT filed Feb. 6, 2015 now issued as U.S. Pat. No. 9,311,520. U.S. patent application Ser. No. 14/419,939 is a national phase application claiming priority to Patent Cooperation Treaty (PCT) Application No. PCT/US2013/035397 entitled METHOD AND APPARATUS FOR PERFORMING AND QUANTIFYING COLOR CHANGES INDUCED BY SPECIFIC CONCENTRATIONS OF BIOLOGICAL ANALYTES IN AN AUTOMATICALLY CALIBRATED ENVIRONMENT filed Apr. 5, 2013. PCT Application No. PCT/US2013/035397 claims the benefit of U.S. Provisional Patent Application No. 61/680,842 entitled MULTI-ANALYTE RAPID DIAGNOSTIC TEST AND METHOD OF USE filed Aug. 8, 2012.

FIELD

The embodiments generally relate to apparatus, systems, and methods for detecting the presence or absence of a variety of analytes in a fluid sample using a diagnostic instrument.

BACKGROUND

Reagent dipsticks and immunoassays have been used in medical clinics for decades in connection with methods for rapidly diagnosing health conditions at the point of care. In a clinical environment, dipsticks have been used for the diagnosis of urinary tract infections, preeclampsia, proteinuria, dehydration, diabetes, internal bleeding and liver problems. As is known, dipsticks are laminated sheets of paper containing reagents that change color when exposed to an analyte solution. Each reagent test pad on the dipstick is chemically treated with a compound that is known to change color in the presence of particular reactants. For example in the context of urinalysis, the dipstick will typically include reagent pads for detecting or measuring analytes present in a biological sample such as urine, including glucose, bilirubin, ketones, specific gravity, blood, pH, protein, urobilirubin, nitrite, leukocytes, microalbumin and creatinin.

The magnitude of this color change is proportional to analyte concentration in the patient fluid. Dipsticks are typically interpreted with the naked eye by comparing the test strip against a colored reference chart. However, such color comparison can cause user confusion and error, for several reasons including changes in ambient lighting, and that a significant portion of the population has impaired color vision.

Automatic methods and apparatus for interpreting test results of dipsticks and immunoassays, which have been exposed to a sample solution, are known in the art. For example, U.S. Patent Application Publication No. 2012/63652 to Chen and all (hereinafter "the '652 publication") discloses a method for color-based reaction testing of biological materials, albeit in an un-calibrated environment, by capturing a digital image of both a test strip and a colored reference chart side by side in a single image. The test results for the test strip are automatically obtained by performing simple color matching between the reacted regions of the test strip and the color reference chart to determine analyte concentration of the biological material.

When employing the method disclosed by the '652 publication, a user must properly align the test strip and the color reference chart before capturing the digital image. Therefore, a user must come into contact with the exposed test strip, after it is soiled by biological samples, such as urine, blood, or feces, and place it in an appropriate position relative to the color reference chart. Therefore, to assist in placement of the test strip and/or chart, automatic interpretation apparatus often include an additional positioning element, such as a box or carpet, to position both the test strips and the chart in the correct orientation.

In view of the problems with presentably available methods for automatically reading test strips, there is a need for an automated testing method, which uses a digital image captured in an un-calibrated environment. The system or method should be configured to automatically calibrate the digital image to correct any color deficiencies, artifacts, or other ambiguities. The method should also automatically identify the relevant portions of the digital image, regardless of how the test strip and/or color reference are positioned in the digital image. Finally, the method should minimize manipulation of samples soiled with biological fluids. The presently invented method and system address these deficiencies of known automatic detection devices, systems, and methods.

SUMMARY

Generally provided are a method and electronic user device for performing quantitative assessment of color changes induced by exposure of multiple test strips to a biological material/fluid. Preferably, the provided system and method permits automatic calibration of a digital image of a plurality of test media which have been exposed to a sample solution, for the purpose of determining whether certain analytes are present or absent from the sample solution. More preferably, one or more embodiments provide a method and electronic user device to quantify color changes induced in various test strips by exposure to the sample. This quantification is based on an automatic calibrating protocol, independent of variations in the external environment. The embodiments can yield accurate, precise, and cost effective measurements while minimizing the user interaction with biological samples. This method is designed to support medical scientific instruments complying with FDA and EU regulations in the field aimed at minimizing errors.

Therefore according a preferred and non-limiting embodiment, a computer-implemented method for quantifying color change of at least one test medium on a diagnostic instrument is provided. The method includes the step of capturing a digital image of at least a portion of the diagnostic instrument, which has been exposed to a biological sample. The diagnostic instrument includes at least one color reference comprising a plurality of reference samples of different colors and at least one test medium containing a reagent, which changes color in the presence of particular analytes in the biological sample. The method further includes the following steps: identifying at least one of the reference samples for the at least one medium in the diagnostic instrument; determining a dominant camera-captured color of a reference sample and a dominant camera-captured color of the at least one test medium; color correcting the dominant camera-captured color of the at least one test medium based on a correction factor derived at least in part from the dominant camera-captured color of the reference sample to determine a corrected test medium color; and comparing the corrected test medium color to a set of possible test medium colors corresponding to predetermined analyte concentrations to determine a test result including an analyte concentration of the biological sample being tested.

In accordance with a further embodiment, a computer-implemented method for determining a relative position on a diagnostic instrument includes the step of capturing a digital image of at least a portion of the diagnostic instrument, which has been exposed to a biological sample. The diagnostic instrument includes at least one test medium containing a reagent, which changes color in the presence of particular analytes in the biological sample. The method further includes the following steps: scanning the digital image to identify the position of a predetermined region on the diagnostic instrument; identifying the at least one test medium on the digital image based at least in part on the position of the predetermined region; and determining a test result by comparing the color of the at least one test medium to a set of possible test medium colors corresponding to predetermined analyte concentrations to determine an analyte concentration of the biological sample being tested.

In accordance with a further embodiment, a method for validating a diagnostic instrument includes the step of capturing a pre-use digital image of at least a portion of the diagnostic instrument, prior to exposing the diagnostic instrument to a biological sample. The diagnostic instrument includes at least one color reference comprising a plurality of reference samples of different colors and at least one test medium containing a reagent, which changes color in the presence of particular analytes in the biological sample. The method further includes the following steps: identifying the at least one test medium in the pre-use digital image of the diagnostic instrument; comparing a color of the at least one test medium to a set of possible test medium colors for reagents, which have not been exposed to an analyte; and determining whether the diagnostic instrument is in condition for use based at least in part on the color of the at least one test medium.

In accordance with a further embodiment, a diagnostic instrument for identifying a plurality of test results by testing a single patient fluid is provided. The instrument includes: an instrument housing; a color reference comprising a plurality of reference samples of different colors affixed to or associated with the housing for determining the test results from a digital image of the diagnostic instrument; and a plurality of test media affixed to the housing containing color-changing reagents, which change color in the presence of particular analytes in a biological sample.

In accordance with a further embodiment, a system for performing diagnostic tests of a biological sample is provided. The system includes a diagnostic instrument and a portable electronic device having a camera sensor for capturing a digital image of at least a portion of the diagnostic instrument and a processor. The diagnostic instrument includes a color reference having a plurality of reference samples of different colors and a plurality of test media containing reagents, which change color in the presence of particular analytes in the biological sample. The processor of the portable electronic device is configured to: identify at least one of the reference samples and at least one of the test media on the digital image of the diagnostic instrument; determine a dominant camera-captured color of a reference sample and a dominant camera-captured color of at least one test medium; color correct the dominant camera-captured color of the at least one test medium based on a correction factor derived at least in part from the dominant camera-captured color of the reference sample to determine a corrected test medium color; and compare the corrected test medium color to a set of possible test medium colors corresponding to predetermined analyte concentrations to determine a test result including an analyte concentration of the biological sample being tested.

In accordance with a further embodiment, a portable electronic device for analyzing a digital image of a diagnostic instrument is provided. The diagnostic instrument includes at least one color reference having a plurality of reference samples of different colors and at least one test medium containing a reagent, which changes color in the presence of particular analytes in the biological sample. The portable electronic device includes: at least one processor; at least one display device; at least one camera sensor; and at least one computer-readable medium including program instructions. When executed by the at least one processor, the programming instructions cause the portable electronic device to: capture a digital image of at least a portion of the diagnostic instrument, which has been exposed to a biological sample, with the camera sensor; identify at least one of the reference samples for the at least one medium in the diagnostic instrument; determine a dominant camera-captured color of a reference sample and a dominant camera-captured color of the at least one test medium; color correct the dominant camera-captured color of the at least one test medium based on a correction factor derived at least in part from the dominant camera-captured color of the reference sample to determine a corrected test medium color; and compare the corrected test medium color to a set of possible test medium colors corresponding to predetermined analyte concentrations to determine a test result including an analyte concentration of the biological sample being tested.

These and other features and characteristics of the embodiments, as well as the methods of operation and functions of the related elements of structures and the combination of parts and manufacture of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the embodiments. As used in the specification and the claims, the singular form of "a", "an", and "the" include plural referents unless the context clearly dictates otherwise.

BRIEF DESCRIPTION OF THE DRAWINGS

For the purpose of facilitating understanding of the embodiments, the accompanying drawings and description illustrate embodiments thereof, its various structures, construction, methods of operation, and many advantages that may be understood and appreciated.

FIGS. 6A-6D are photographic representations of a diagnostic instrument with markings to indicate the orientation of the instrument in the photograph relative to the x-axis, the y-axis, or the z-axis.

FIG. 8 is a magnified photographic representation of a reference color bar as identified by the geographic correction calculations, of the method of FIG. 4.

FIG. 14 is one embodiment of a decision tree for identifying patient conditions related to increased urine leucocytes.

FIG. 15 is one embodiment of a decision tree for identifying a patient condition related to an increase in urinary proteins.

DETAILED DESCRIPTION

Figure 1:
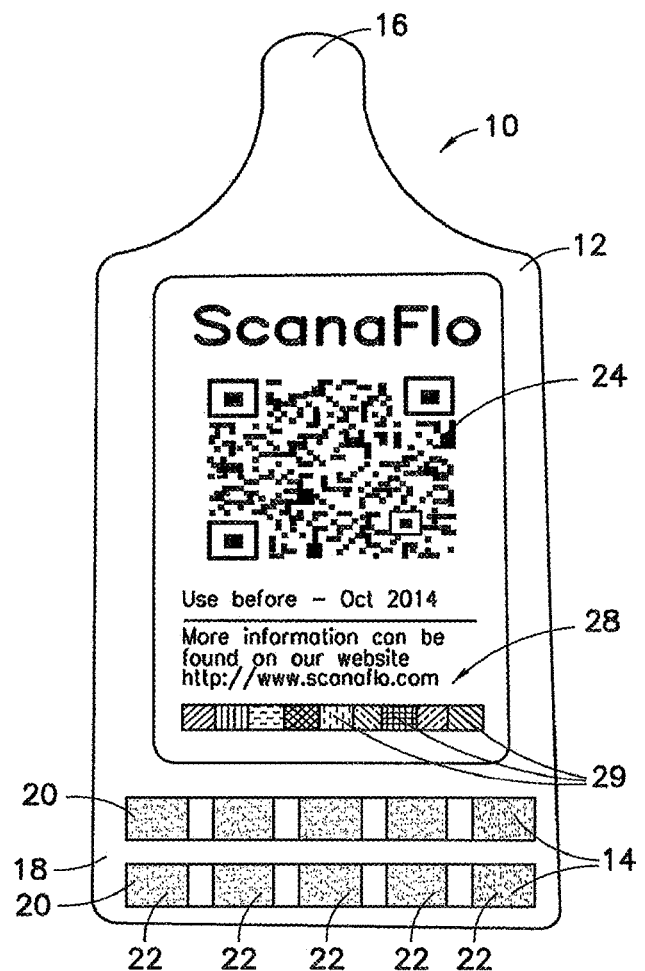
FIG. 1 is a top view of one embodiment of a diagnostic instrument.

For purposes of the description hereinafter, the terms "upper", "lower", "right", "left", "vertical", "horizontal", "top", "bottom", "lateral", "longitudinal", and derivatives thereof shall relate to the embodiments as it is oriented in the drawing figures. However, it is to be understood that the embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that may be wired and/or wireless in nature. Additionally, two units or components may be in communication with each other even though the data transmitted may be modified, processed, and/or routed between the first and second unit or component. For example, a first unit may be in communication with a second unit, even though the first unit passively receives data, and does not actively transmit data to the second unit. As another example, a first unit may be in communication with a second unit if an intermediary unit processes data from one unit and transmits processed data to the second unit. It will be appreciated that numerous other arrangements are possible. The components or units may be directly connected to each other or may be connected through one or more other devices or components. The various coupling components for the devices can include but are not limited to, the Internet, a wireless network, a conventional wire cable, an optical cable or connection through air, water or any other medium that conducts signals, and any other coupling device or medium.

One or more embodiments are drawn to diagnostic instruments, systems and methods of use thereof for testing of a patient fluid sample, which can be used either in clinical settings or for home use. More particularly, one or more embodiments relate to the performance of color-based reaction testing of biological material in an automatically calibrated environment. Some embodiments are implemented as a software application (an "App") running on a portable electronic device, such as a cell phone, tablet PC, computer, laptop, or other dedicated electronic device. The method has been designed to minimize user contact and manipulations of biologically soiled samples. Error prevention and compliance with medical instrument regulations have been implemented at all levels in the design of protocols. In particular the invented methods have been designed avoid modifying, compromising, and discarding raw data.

The diagnostic instrument is configured to provide rapid detection of patient conditions using test strips, such as reagent dipsticks. Dipsticks are typically narrow strips of plastic or paper having certain reagents or antibodies that act as recognition elements to detect a given analyte or disease marker in a patient fluid sample. Often, the intensity of a color change of the test strip is an indication of the concentration of the analyte or disease marker in the patient fluid. Patient fluid may include a urine sample, blood sample, patient cells disposed in a fluid solution (e.g. cells obtained from a throat swab), semen, mucous, blood, saliva, and the like.

The diagnostic instrument is configured to test a patient fluid sample for a variety of diseases and patient conditions to increase the likelihood that a variety of conditions may be identified during a testing activity. Thus, the user will not need to select which test to perform or the order in which tests should be performed. In one non-limiting embodiment, the diagnostic instrument may test for pregnancy and pregnancy complications, such as preeclampsia.

With reference to FIG. 1, and in one preferred and non-limiting embodiment, provided is a diagnostic instrument 10, including a paddle 12 for holding at least one test strip 14. The paddle 12 includes a handle 16 and a testing region 18 adapted to hold a plurality of test strips 14. The testing region 18 includes a plurality of indentations 20 for holding at least one individual test strip 14. The test strip 14 may be a reagent dipstick. In that case, each test strip 14 includes a plurality of test media, such as chemical test pads (CTP) 22, containing a color-changing reagent for identifying the concentration of certain analytes in a patient fluid, such as urine, blood, or saliva. The user exposes the diagnostic instrument 10, including the test strips 14, to the fluid sample by dipping the instrument 10 into the patient fluid sample to submerge the test strips 14. As is shown in FIG. 1, more than one test strip 14 can be affixed to the paddle 12, thus increasing the number of analytes that can be tested. In certain embodiments, the paddle 12 allows for testing of a number of analytes simultaneously.

A diagnostic instrument 10 which allows a user to test a signal fluid sample for a variety of patient conditions is intended to reduce user anxiety and to inspire confidence in individuals without medical training and with limited experience in performing medical tests. More particularly, the diagnostic instrument 10 tests for a plurality of patient conditions, meaning that the user does not need to select an appropriate test or determine which conditions are most likely to be present. Instead, in a single testing activity, the user tests for a plurality of conditions using a single fluid sample exposed to a single diagnostic instrument 10. Furthermore, the diagnostic instrument 10 includes the paddle 12 and the handle 16, making the diagnostic instrument 10 easies for a user to maneuver. Similarly, the handle 16 ensures that the user is protected from contacting the fluid sample during the test. Therefore, a user may confidently perform the test, using the diagnostic instrument 10, without worrying that he or she will accidently contact patient fluid. Additionally, the diagnostic instrument 10 is intended to be provided with clear and easy-to-understand instructions for performing the test and interpreting the results, to ensure that the untrained user receive accurate diagnostic information from the tests that are being performed.

With continued reference to FIG. 1, the diagnostic instrument further includes a color reference, such as a reference color bar (RCB) 28, disposed on the diagnostic instrument 10. The RCB 28 includes a plurality of color samples 29 in a side-by-side linear arrangement. For example, the RCB 28 may include color samples 29 for one or more of the following colors: Cyan, Magenta, Yellow, Key (black), Gray, White, Red, Green, Blue. The color sample 29 colors correspond with common color spaces, such as Red-Green-Blue, Cyan-Magenta-Yellow-Key (CMYK), pantone, Munsell, International Commission on Illumination (CIE) XYZ, or the International Color Consortium (ICC) device independent color space (L*a*b color space). The RCB 28 is used for image processing, specifically to calibrate a digital image of the diagnostic instrument 10 to improve the quality and accuracy of color analysis.

In certain preferred and non-limiting embodiments, the diagnostic instrument 10 further includes an identification label, such as a unique identification (UID) 24. The UID may be a visual indicia serving as a landmark to identify a specific area of the diagnostic instrument. Additionally, the UID 24 may be configured to contain certain identification information about the diagnostic instrument 10, such as a list of the analytes that are being tested, expiration date of the instrument 10, the conditions that are being tested, and other identifying information. The information may be printed directly on or encrypted with the UID 24, such as is the case with a label or two-dimensional bar code, such as a QR code. Alternatively, the UID 24 may be associated with information stored elsewhere (e.g., server accessible over the internet), such as is the case with bar codes for example. The identification information may be used in validation processes to ensure the diagnostic instrument 10 is suitable for the tests being performed and to ensure that it is safe to use, in good working condition, or to resolve other issues which may impact quality and reliability of the test results. It is noted that methods for automatically analyzing test strips in the prior art do not include these steps for validating the diagnostic instrument.

The diagnostic instrument 10 is configured so that a digital image of the instrument may be captured using a portable electronic device such as a smart phone. The diagnostic instrument 10 is easier to use than diagnostic instruments of the prior art, such as test strips disclosed in the '652 publication. Specifically, unlike previously known systems and methods, a user does not need to handle the used test strips, soiled by biological samples such as urine, blood, feces, etc., because the used diagnostic instrument does not need to be placed in side by side arrangement with an interpretation table, such as a manufacturer's interpretation color chart (MICC), when obtaining the digital image. Additionally, since the diagnostic instrument 10 does not need to be placed next to corresponding MICC, there is no possibility of using the wrong MICC for a particular diagnostic instrument (e.g. reading strips from manufacturer A with a MICC from manufacturer B).

Having described the structure of an embodiment of the diagnostic instrument 10, a system 100 for performing diagnostic tests on a biological sample using the diagnostic instrument 10 will now be described.

Figure 2:
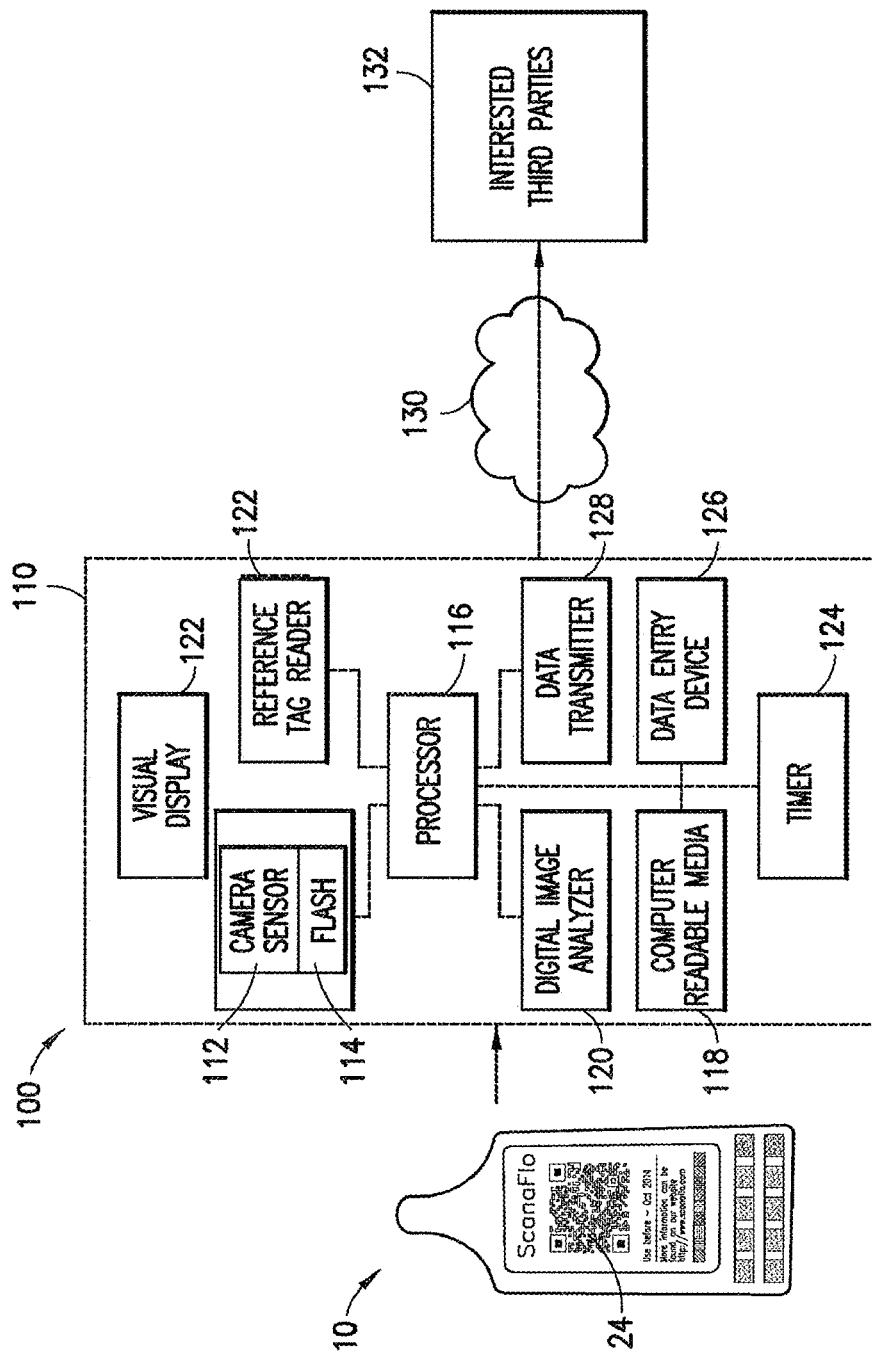
FIG. 2 is a schematic view of one embodiment of a system for analyzing a biological sample using the diagnostic instrument of FIG. 1.

With reference to FIG. 2, a system 100 for performing diagnostic tests on a biological sample includes the diagnostic instrument 10 and a portable electronic device 110. Generally, and in various preferred and non-limiting embodiments, the system 100 is used for acquiring, evaluating, analyzing, processing, and/or presenting image data of a diagnostic instrument 10 obtained by the portable electronic device 110. The system 100 may be used in any type of medical analytical/diagnostic setting, including at a medical clinic, at an off-site laboratory, or home use without medical supervision. It should be understood that different aspects of the embodiments can be appreciated individually, collectively, or in combination with each other. In addition, image data may include any type or form of visual, video, and/or observable data, including, but not limited to, a discrete image, a sequence of images, one or more images from a video, a video sequence, and the like.

The portable electronic device 110 could be any kind of smartphone (e.g., APPLE IPHONE, BLACKBERRY), handheld computer (e.g., APPLE IPAD), or any type of personal computer, network computer, workstation, minicomputer, mainframe or the like running any operating system, such as any version of ANDROID, LINUX, WINDOWS, WINDOWS NT, WINDOWS 2000, WINDOWS XP, MACOS, UNIX, SOLARIS, ARM OR IOS operating systems.

In certain non-limiting embodiments, the portable electronic device 110 includes a camera sensor 112, for obtaining the digital image of the diagnostic instrument. Certain sensor array chips are presently available with varying properties, with CCD (Charge Coupled Device) and CMOS (Complementary Metal Oxide Conductor) representing the most common camera sensor chips. Each chip technology offers advantages and these evolve relatively with improving designs. In summary, a CCD offers a larger energy capture fraction and serial read-out with minimal local processing, whereas a CMOS has addressability and processing capability for each pixel, but with some loss of sensitivity. The portable electronic device 110 may further include a flash 114 for improving the quality and readability of images captured with the camera sensor 112.

Hereinafter, the system 100 is described in terms of functional components and various processing steps. It is noted that the functional blocks may be realized by any number of hardware and/or software components configured to perform specified functions. In a preferred and non-limiting embodiment, the functional components and processing steps are associated with and/or performed using the portable electronic device 110. For example, the embodiments may employ various integrated circuit components (e.g., memory elements, processing elements, logic elements, lookup tables, and the like), which may carry out a variety of functions under the control of one or more processors or other control devices. Similarly, the software components of the embodiments may be implemented with any programming or scripting languages such as C, C#, C++, JAVA, assembler, extensible markup language (XML), or extensible style sheet transformations (XSLT). The various algorithms may be implemented with any combination of data structures, objects, processes, routines, or other programming elements.

With continued reference to FIG. 2, in one non-limiting embodiment, it is envisioned that the functional components and processing steps will be included with and/or performed using the portable electronic device 110. In that case, the portable electronic device 110 includes a processor 116 configured to execute program instructions stored on computer-readable media 118 associated with the portable electronic device 110. For purposes of the present discussion, computer-readable media 118 may include computer storage media, such as media implemented in any method or technology for storage of information, such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by an electronic device, such as portable electronic device 110.

In certain non-limiting embodiments of the program, the processor 116 controls a digital image analyzer 120 for identifying regions of a digital image containing relevant data, color correcting the digital image, and comparing the corrected portions of the digital image to table entries of the MICC to determine test results. The processor 116 may further control a reference tag reader 122 configured to identify and extract information from a UID 24 affixed to or associated with the diagnostic instrument 10. The processor 116 may further control a display 122, connected to or associated with the portable electronic device 110, for presenting information such as instructions for using the diagnostic instrument and test results to a user. The processor 116 may also control a timer 124 for measuring the time between when the diagnostic instrument 10 is exposed to a fluid sample and when the digital image of the diagnostic instrument 10 is captured. Additionally, in certain embodiments, the processor 116 controls a data entry device 126 allowing a user to enter additional information, including patient history information, symptoms, and physical characteristics of the user. The data entry device 126 may include any input device or user interface as is known in the art, which allows a user to control an electronic device including, but not limited to, gestures on a touch-screen or any other actions that cause a change in readings obtained from sensors, keypad presses, and the like.

In addition to storing the program for controlling functions of the portable electronic device 110, the computer-readable media 118 may also store data including a plurality of MICC tables used to determine test results. The computer readable media 118 may also store raw or pre-processed images obtained by the camera sensor 112, decision trees for determining a patient condition, and other input data necessary for executing functions of the program. Additionally, the computer-readable media 118 may include communications media, such as computer-readable instructions, data structures, program modules, or other data in other transport mechanisms and include any information delivery media, wired media (such as a wired network and a direct-wired connection), and wireless media. Computer-readable media may include all machine-readable media with the sole exception of transitory, propagating signals. Of course, combinations of any of the above should also be included within the scope of computer-readable media.

Additionally, it is to be recognized that some or all of the functions, aspects, features, and instances of the embodiments may be implemented on a variety of computing devices and systems, wherein these computing devices include the appropriate processing mechanisms and computer-readable media for storing and executing computer-readable instructions, such as programming instructions, code, and the like. The functional aspects of a software application (App) for directing the function of a portable electronic device will be discussed in greater detail in connection with methods for using the diagnostic instrument to identify a patient condition and methods of image processing of a digital image of the diagnostic instrument.

In a further non-limiting embodiment, the system 100 includes a data transmitter 128 for transmission of data and information from the portable electronic device 110 to an external electronic device, a computer network, and/or a digital storage device, collectively referred to as a network environment 130, known colloquially as "the cloud". Once the data is provided to the network environment 130, it may be made available to interested third parties 132, including caregivers, doctors, third party payment organizations, insurance and health maintenance organizations, pharmacists, or public health organizations.

Having described the diagnostic instrument 10 and a system including the diagnostic instrument 10 and the portable electronic device 110, methods for using the diagnostic instrument and obtaining test results will now be discussed in further detail.

Figure 3:
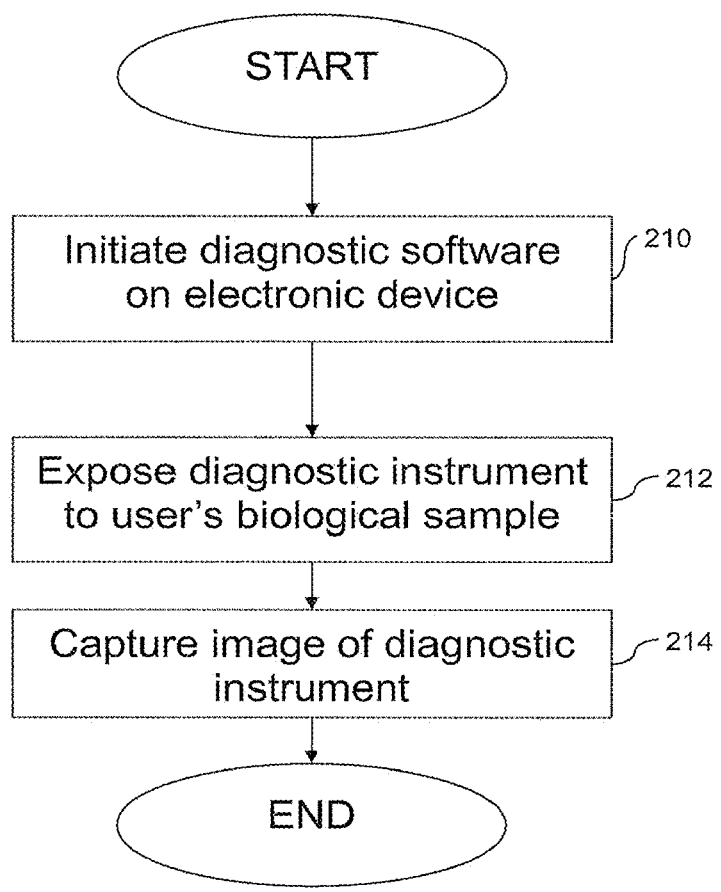
FIG. 3 is a flow chart of an embodiment of a method for capturing an image of a diagnostic instrument.

Initially, as depicted in FIG. 3, a method for obtaining a digital image of the diagnostic instrument is depicted. A user begins by installing the software program configured to acquire and analyze a digital image of the diagnostic instrument on a portable electronic device. Once the software program is installed, the user initiates the program 210, by an active activation means such as by pressing a "Begin" button on the display screen of the portable electronic device. Alternatively, the program 210 may be automatically activated. The user then exposes 212 the diagnostic instrument to a biological sample, which exposes the plurality of CTP to analytes contained in the sample and begins a chemical reaction between the CTP and analytes. In certain embodiments, a timer is started when the diagnostic instrument is exposed to the sample. After a predetermined time passes, the portable electronic device prompts the user to capture the digital image of the diagnostic instrument. The timing when the digital image is captured is critical because colors of the CTP continue to change over time. Therefore, missing this acquisition window may void any test results from the diagnostic instrument. Alternatively, additional calculations may be performed to compensate for the incorrect exposure time.

The user captures 214 the digital image of the diagnostic instrument 10 using the camera sensor of the portable electronic device. In certain embodiments, the portable electronic device may provide instructions for obtaining the digital image, such as by suggesting a preferred camera position or lighting environment. For example, in certain embodiments, when preparing to capture the digital image of the diagnostic instrument, the user interface superimposes a virtual contour of the diagnostic instrument onto the real image acquired by the camera sensor in video mode. The user is then asked to overlay the virtual contour with the image of the diagnostic instrument and to take the picture precisely when indicated by the timer. When the user triggers the camera shutter, the camera is configured to switch from video to a high resolution mode to capture a high resolution single frame image of the diagnostic instrument. The captured digital image includes at least a portion of the RCB, the CTP, and/or the UID of the diagnostic instrument. More particularly, a high definition image of the diagnostic instrument is captured preferably under flash or other standardized illumination conditions (if available) so as to provide the most reproducible lighting conditions.

Figure 4:
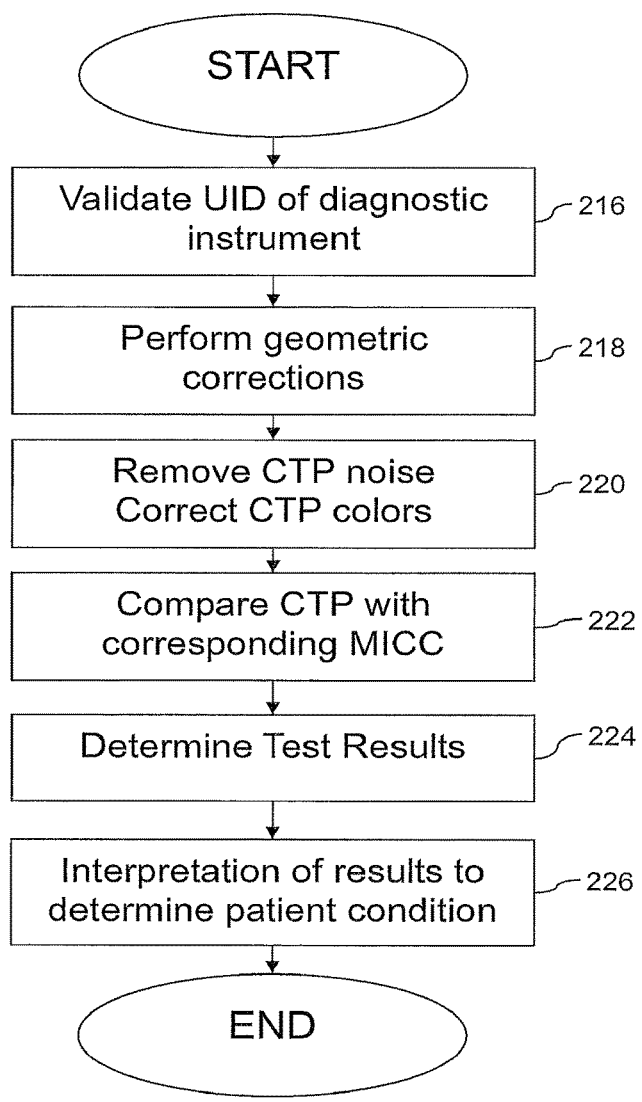
FIG. 4 is a flow chart of an embodiment of a method for determining a patient condition from a digital image of a diagnostic instrument.

In certain non-limiting embodiments and with reference to FIG. 4, once the digital image of the diagnostic instrument is obtained, the portable electronic device may be used to validate 216 the diagnostic instrument. Specifically, an optical reader (e.g. bar code, matrix bar code reader, two-dimensional bar code reader, or a QR code reader), associated with the portable electronic device, is used to scan the captured digital image to locate the UID. The UID includes or corresponds to information about the diagnostic instrument being tested. The software is configured to ensure that the diagnostic instrument is safe for use and suitable for a specific application, based on the identification information from the UID. Additionally, the UID validation step may include using the identification information from the UID to select the correct MICC, from available options stored on the portable electronic device, for use in analyzing the results of the diagnostic instrument being tested.

Following the validation step 216, geometric corrections are performed 218 to determine the position of the other elements, namely the RCB and CTP, of the diagnostic instrument based on the position and orientation of the UID. Geometric corrections compensate for a large range of user positioning and attitude errors, which may occur as the user holds the instrument to capture the digital image. The geographic corrections may be defined in terms of pitch, roll, and yaw angles of the diagnostic instrument in the digital image. Based on the geometric correction, the position of the RCB and CTP can be effectively identified. The method further includes applying local image corrections to the identified portions of the digital image including the RCB or CTP, such as analyzing the digital image to apply spatial guard bands around and just within the boundary of each identified area.

With continued reference to FIG. 4, after the digital image is obtained and the geometric corrections performed, the digital image is processed to remove image noise and to correct image coloration 220. It is noted that all of the operations, corrections, calculations, and modifications are performed on a stored copy of the high-definition image. In this way, the raw image is separately maintained and can be used for later analysis, if necessary. More specifically, the color correction process corrects colors of the portion of a copy of the captured image including the CTP, based on the calibration measurements and correction offset determined from analysis of the portion of the digital image including the RCB.

Figure 5:
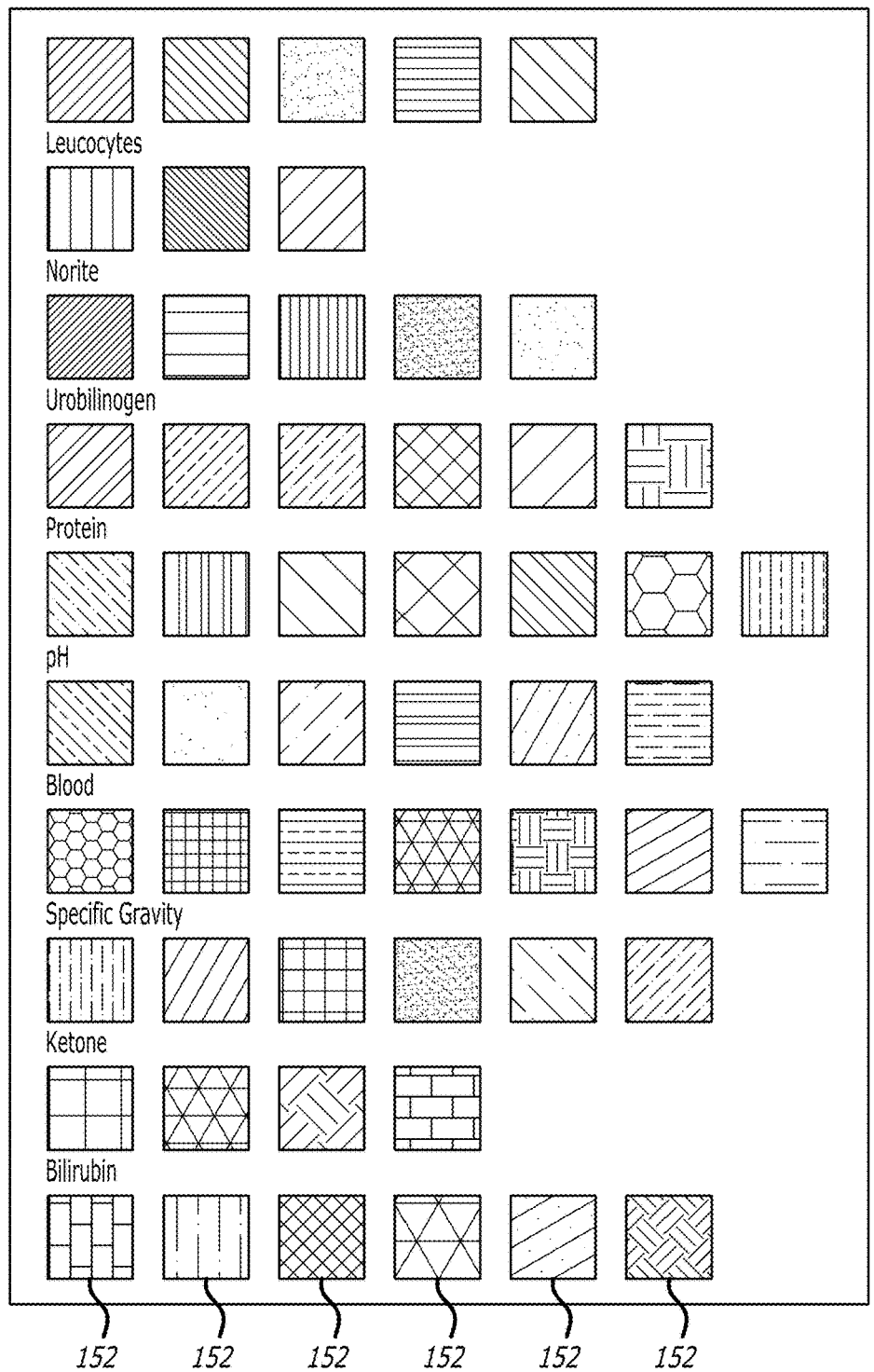
FIG. 5 is a schematic view of a Manufacturing Interpretation Color Chart (MICC) for use in urinalysis with colors that can be captured by the diagnostic instrument.

Once the portions of the digital image including the CTP are color corrected, the corrected colors can be compared 222 with color samples from the MICC. As is described in greater detail below, comparison between the CTP color change and the MICC is based on an interpolation process. The MICC is a table depicting a plurality of possible results (e.g. color samples) for one or more of the CTP on the diagnostic instrument. An exemplary MICC 150 for use with a standard test strip is depicted in FIG. 5. The MICC 150 includes a plurality of color samples 152 corresponding to the range of possible color changes of the CTP being tested. The various color samples correspond to CTP color change over a range of analyte concentrations or titration level (e.g. absent, normal, positive, very positive . . . ). The MICC 150 is typically provided by the manufacturer of the test strip being tested. With continued reference to FIG. 4, based on the comparison between the corrected CTP color and the MICC color samples, the test results (e.g. concentration or titration level) can be determined 224.

Another way of calibrating such color trajectories would be to generate an absolute calibration curve comprising numerous points (5, 6, 7 to 20, 30, 40 preferably 12) made of the absolute color measurements obtained at known analyte concentrations. This is done for every CTP. This generates an absolute color curve (ACC) for a CTP associated with an analyte, such as shown by the color trajectory line 424 in FIG. 10, for example, or the interpolated color trajectory 428 shown in FIG. 20, for example. The continuous color trajectories enable quantitative measurements instead of bracketed measurements. The absolute color curve (ACC) may be simply referred to herein as a color trajectory.

For certain embodiments, the predetermined manufacturer's interpretation color chart values and the absolute color curve values (MICC/ACC) are also used to provide confirmation that the diagnostic instrument provides valid results and is suitable for use. More particularly, the MICC/ACC represents the range of possible color changes for the CTP. If the color of the identified region does not correspond to a possible test result color, it is assumed that either the wrong MICC/ACC was used to analyze the test results or that the diagnostic instrument was defective. Accordingly, any results falling outside of the color range defined by the MICC/ACC are discarded.

Figure 19A:
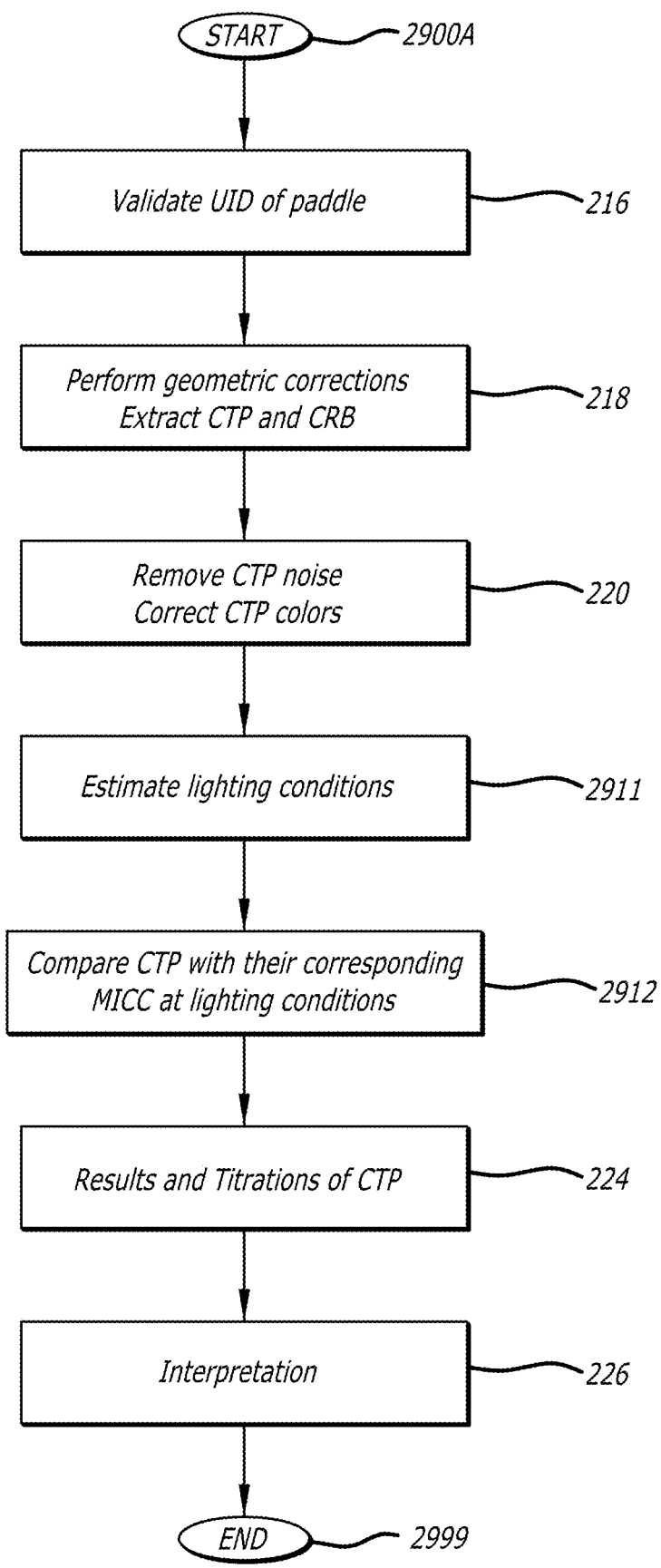
FIG. 19A is a flow chart of an embodiment of a method for determining a patient condition from a digital image of a diagnostic instrument in various lighting conditions, by estimation of ambient lighting to compare the measurements to trajectories taken in similar conditions.

Referring to FIG. 19A, another embodiment extends and generalizes the approach described in FIG. 4 towards use in a larger range of lighting conditions, such as from dim light (about 50 lux) to office lighting (about 500 lux) to studio light (around 1000-1500 lux), for example.

In FIG. 19A, the method begins with step 2900A and continues with the workflow through steps 216, 218 and 220, as was explained with reference to FIG. 4. The process then performs additional steps 2911 and 2912 and then continues through steps 224 and 226, as was explained with reference to FIG. 4.

At step 2911, an estimate of the relative lighting conditions of the reference color bar (RCB) is made. There are a number of methods described in the literature to determine lighting conditions, often relying on parameters of: (i) the luminance L, (illuminance) and/or (ii) the irradiance Ir (radiance).

Luminance L of a reference color bar (RCB) can be calculated by the linear CIE 1931 luminance for ITU-R BT.709 primaries, using the luminance equation $L=0.2126R+0.7152G+0.0722B$, where R, G, B are the camera perceived colors of elements of the RCB. The irradiance Ir of the reference color bar (RCB) can be calculated by the equation $Ir=(R+2G+B)/4$, where R, G, B are the camera perceived red, green, and blue colors of elements of the RCB. The value for luminance L and the value for irradiance Ir can be gamma compensated or not. Luminance estimations may combine the values of luminance L and irradiance Ir into a linear or non-linear function. Values for luminance L and irradiance Ir can be obtained by exposing the RCB to various lighting conditions. Exemplary equations to combine values of luminance L and irradiance Ir to estimate lighting conditions include but are not limited to: gamma differences, linear differences, gamma irradiance differences, linear irradiance differences between black and white RCB elements. In addition, the use of a photometer in a camera, if available, or use of photographic parameters like speed, aperture, and file sensitivity, if available, may also be used to estimate the lighting conditions under which the image for an RCB and a CTP are captured.

At step 2912, with portions of the digital image including the CTP being color corrected previously at step 220, the corrected colors of the CTP can be compared with color samples. The color samples are predetermined from chemical experiments performed with the CTP under known luminance L recreating a complete MICC/ACC under such lighting conditions.

At step 224, results and titration of the CTP are performed in the same manner as was described with reference to FIG. 4, followed by an interpretation step 226. The workflow then goes to process 2999 to either end or continuing to analyze other CTPs that have yet to be analyzed.

Figure 19B:
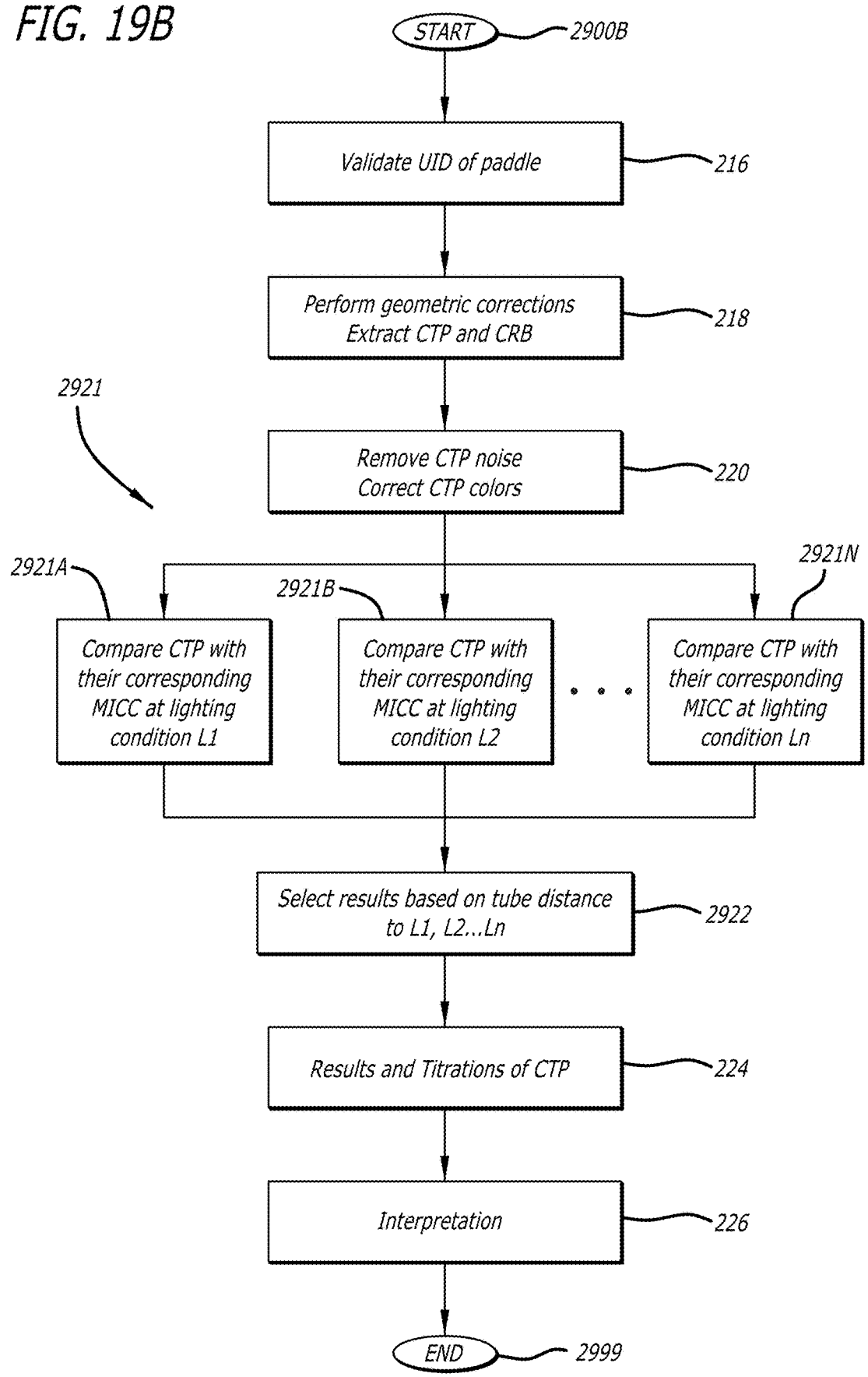
FIG. 19B is a flow chart of an embodiment of a method for determining a patient condition from a digital image of a diagnostic instrument in various lighting conditions, by comparing the measurements to multiple lighting conditions and selecting the best one within the confidence validity tube of a trajectory.

Referring now to FIG. 19B, another method can be used to extend and generalize the method of color quantification for use over a range of different lighting conditions. An image of the CTP and RCB may be captured from dim lighting (about 50 lux) to office lighting (about 500 lux) to studio lighting (around 1000-1500 lux), for example.

In FIG. 19B, the method starts with step 2900B and continues the workflow through steps 216, 218 and 220, as was explained with reference to FIG. 4. Steps 2921 (parallel comparisons 2921A-2921N) and 2922 are then performed. The workflow then continues with steps 224 and 226 as was explained with reference to FIG. 4.

At step 2921, evaluations 2921A-2921N of several lighting conditions L1 through Ln in parallel are made. The RGB color of the CTP is compared against a plurality of reference MICC/ACCs under the plurality of lighting conditions L1 through Ln. For each color trajectory in each luminance of lighting conditions L1 through Ln, a tube of confidence determines the level of confidence of a given measure.

At step 2922, the measure falling within one of the tubes of confidence is deemed a valid measure and is selected as the result of comparison. In case of overlapping tubes there are several valid results which are refined by a result decision making algorithm. Some examples of a result decision making algorithms are: (i) use the trajectory nearest to the point, (ii) use of a linear combination of trajectories according to topology (e.g. weighted combination of multiple trajectory results according to proximity to trajectory), (iii) use of a statistical combination of trajectories (averages and variances to trajectories), (iv) non-linear functions, and (v) votes. The embodiments are not limited to these result decision making algorithms. For example a simple embodiment of a statistical combination is an average between valid results.

At step 224, results and titration of the CTP are performed as was described with reference to FIG. 4 and followed by the interpretation step 226 as was described with reference to FIG. 4.

At step 226, the test results for an individual CTP can be interpreted either individually or in combination with other test results and diagnostic information to determine a patient condition. For example, multiple test results that indicate the presence or absence of a number of different analytes in the biological fluid sample. These multiple test results can be considered in combination to determine a probable patient condition.

Similarly, if the test results suggest a plurality of possible patient conditions, the method may further include asking the user patient various diagnostic questions to rule out certain possible conditions to arrive at a most likely patient condition. In certain embodiments, the test results and/or patient condition information are presented to a user on a visual display device of the portable electronic device. If all the CTPs have been considered and the results interpreted, the process may end at step 2999.

Having generally described methods for using the diagnostic instrument, capturing a digital image of the diagnostic instrument, and for determining test results using a portable electronic device, the various processes, algorithms, and methods for analyzing the digital image will now be described in greater detail. It is understood that the processes described below are intended only as exemplary processes and methods for analyzing a digital image of a diagnostic instrument, and are not intended to limit the scope of the embodiments in any way. Furthermore, it is understood that the described processes may be implemented using the portable electronic device or other computers and processing apparatus as are known in the art.

Validation of the Diagnostic Instrument Based on the UID

As shown in FIG. 4, a non-limiting embodiment of the method includes the step of validating 216 the UID to ensure that the diagnostic instrument is suitable for the test being performed. The validation step requires determining the position of the UID on the digital image of the diagnostic instrument. To determine the UID position, the digital image may be scanned using a digital reader or similar image processing algorithm or device. The scanning function may also be used to ensure that the whole diagnostic instrument is acceptably in focus in the digital image. If the digital image is not properly focused, the user may be asked to obtain a replacement image of the diagnostic instrument.

The UID may be implemented as a matrix or two-dimensional bar code, such as a QR code. In other embodiments, the UID is a bar code or near-field communication tag. The UID includes or is associated with certain identifying information about the diagnostic instrument, including the manufacture date of the diagnostic instrument, the expiration date of the diagnostic instrument, the analytes tested for by the instrument, identifying information about the test subject, or patient condition information. For QR codes and similar visual indicia, the identifying information is embedded expressly on the UID itself. The embedded information can be encrypted using various encryption security mechanisms, as are known in the art. Alternatively, the information on the UID may direct the electronic device or digital reader to information stored on an external device. The UID is read according to standard algorithms that are well known in the art. Optionally, the information about the diagnostic instrument contained on the UID may be used to compare the diagnostic instrument with other available testing instruments to ensure that the diagnostic instrument is compatible with software and hardware of the portable electronic device and is the most suitable testing device available for a given application.

Additionally, the validation operation 216 may be used to ensure that the device was legally obtained and was not tampered with during shipping to a user. For example, the UID may contain information about the manufacturer, source, and traceability (e.g. point of origin of the diagnostic instrument and any third parties that have handled the instrument since it was manufactured) of the diagnostic instrument. If any of the identifying information is suspect or incorrect, the diagnostic instrument may be rejected and the user informed that the diagnostic test cannot be performed. Such validation actions prevent rogue and/or unsafe products from being used, such as products that were sold illegally or were acquired from unlicensed third parties.

Perform Geometric Corrections to Identify CTP and RCB

The method further includes performing geometric corrections 218 on the digital image, taking into account the geometric deformations of the initial image to find the proper CTP and RCB sub-images of the CTP and RCB. The process takes into account the geometric deformations of the initial image to find the proper CTP and RCB sub-images, which are subsequently cropped, as precisely as possible, to remove any edge artifacts from the identified regions of the digital image, leaving only the individual colored areas of the CTP and RCB for further analysis.

When preparing to take pictures, the user interface superimposes a virtual contour of the paddle onto the real image acquired by the camera in video mode prior to single frame acquisition in high resolution camera mode. The user is asked to overlay the virtual contour with the image of the paddle and to take the picture precisely when indicated by the timer in the application.

When the user triggers the camera shutter, the camera switches from video to high resolution mode to capture the best possible image of the paddle, improving the precision of the method described in this patent application.

Specifically, the geometric corrections are based on the position of the UID in the digital image. Initially, the position of the UID is identified by scanning the digital image, as is described above in connection with the validation process. With reference to FIGS. 6A-6D, in certain embodiments of the method, four UID 24 points A, B, C, D are identified on the corners of the UID 24 to form a square of known dimensions that encloses the UID 24. Based on the orientation of the UID 24 in the digital image, the vertical (X-scale) and horizontal (Y-scale) scales, as well as, scale factors, including the yaw, pitch, and roll, of the diagnostic instrument 10 are calculated. Based on the calculated position of the UID 24 and scale factors, a theoretic location of the CTP 22 and the RCB 28 can be calculated. The calculated theoretic positions are identified on the digital image. Identification of the CTP and RCB allows for extraction of CTP and RCB sub-images from the digital image of the diagnostic instrument 10. The calculations required to determine the theoretic locations are described herein. Notations used in the following are:

$$A(x,y) = Ax, Ay$$

$$Ti(x,y) = Tix, Tiy$$

With reference to FIG. 6B, the yaw angle (rotation around Z axis) is directly measured in the image by:

$$\text{yawAngle} = a\,\tan((Ay-Dy)/(Ax-Dx))$$

and the positions are corrected through a rotation around point A, creating a new referential X' and Y'.

With reference to FIG. 6C, the pitch angle (rotation around Y axis) is approximated by the difference of length between AB and DC projections on axis Y'.

$$\text{Pitch approximation} = \text{abs}(Dy-Cy)/\text{abs}(Ay-By)$$

$$\text{Pitch correction} = (\text{abs}(Dy-Cy)/\text{abs}(Ay-By))^3,$$

With reference to FIG. 6D, the roll angle (rotation around X axis) is approximated by the angle between axis Y' and AB or DC segments $$DC\text{Angle} = a\,\tan((Cx-Dx)/(Cy-Dy));$$

The composite correction for both roll and yaw is calculated as:

$$\text{AngFact} = \sin(DC\text{Angle}) + \sin(\text{yawAngle});$$

The coordinates of the CTP 22 are calculated by applying the following corrections to points T1 ... Tn defined in FIG. 6A to obtain its transformation TA.

$$TAy=\text{round}(Tiy*Yscale);$$

$$TAx=\text{round}(Tix*Xscale-AngFact*TAy);$$

The coordinates of the RCB 28 can be calculated using the same equations, thereby providing a theoretic location of the RCB 28 on the digital image.

Removing CTP Noise and CTP Color Correction

Figure 7A:
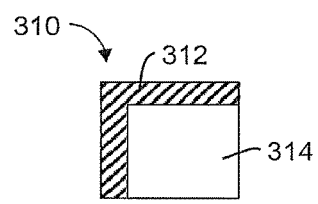
FIGS. 7A-7C are schematic representations of magnified views of color test pads including background artifacts, as identified by the geometric correction calculations of the method of FIG. 4.
Figure 7B:
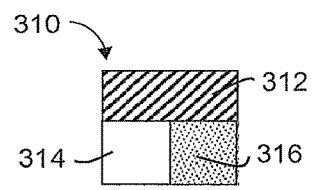
Figure 7C:
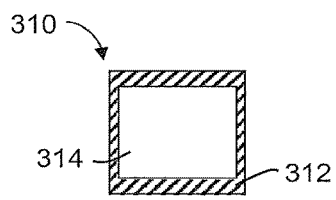

With continued reference to FIG. 4, the CTP image identified by the geometric calculations may not be perfect for various reasons. Therefore, once the CTP and RCB sub-images are identified and extracted by the geometric corrections, processes are implemented to remove CTP noise and to correct the colors 220 of the digital image to accurately reflect the coloration under standard lighting conditions. It is understood, however, that the calculated theoretic positions of the CTP and RCB, and resulting extracted sub-images, may not be accurate and align exactly with the RCP and CTP, for a variety of reasons. With reference to FIGS. 7A-7C, background artifacts 312, from the housing of the diagnostic instrument 10, may incorrectly be included within the CTP sub-image 310 identified by the geometric correction calculations, described above. The background artifacts 312 are adjacent to or surround the actual CTP image 314. As shown in FIG. 7A, background artifacts 312 are present at the left and top of the CTP sub-image 310. FIG. 7B has a large inclusion of a background artifact 312 on top and a second background artifact 316 to the right of the actual CTP image 314. FIG. 7C includes a smaller marginal background artifact 312 surrounding the actual CTP region 314. The background artifacts 312, 316 may be removed by applying a local image correction, in which spatial guard bands are placed around and just within the boundary of the actual CTP image 314. Background artifacts 312, 314 outside of the region enclosed by the guard bands are removed from the CTP sub-image. The more uniform color patch (e.g. the actual CTP image 314) within the guard band is then filtered and optimized to improve image quality.

With reference to FIG. 8, due to the length and inclination of the RCB sub-image 318 extracted from the digital image of the diagnostic instrument 10, the RCB 28 is also typically not accurately identified by the geometric correction calculations. For example, the RCB sub-image 318 may include background lines 320 of noise on top and bottom of the actual RCB image 322, as shown in FIG. 8. Accordingly, an additional step of removing the background lines 320 from the sub-image 318 to accurately identify the RCB 28 is required. This operation is performed by applying a variance operator line by line over the RCB sub-image 318. A longitudinal line across the RCB sub-image 318 with a low variance is not part of the RCB 28 and can be deleted. However, lines running across the actual RCB image 322 would have a high and well known variance. Thus, such high variance lines are not filtered out and are presumed to capture the actual RCB image 322.

Additional image imperfections including noise from the camera sensor, artifacts caused by changing lighting conditions, imperfections of the samples themselves, variations in the CTP chemical reactions, or any combination thereof may also be present in the actual CTP and RCB images 314, 322, even after the background artifacts 312, 316 and background lines 320 are removed. These imperfects may be removed by filtering and color correction. However, the challenge in filtering noise in medical applications is to avoid tampering with the raw data. This is particularly true in the color space where classic signal processing methods, such as linear filtering, might contaminate or distort samples and create questionable results. For example, a single red pixel averaged over a white area introduces low level pink that that could be misinterpreted as a test result. The Nitrite CTP is a good example where the slightest detection of pink corresponds to a positive result. Therefore, the filtering method is based on a sorting operation that does not modify the raw data and does not introduce colors into existing points, even at infinitesimal levels. Additionally, the quality of the identified CTP region is further improved by conditionally rejecting anomalous color points, which fall far outside of the nominally uniform color across the test panel. Such conditional rejection of outlier points presents a significant improvement in reducing error without altering raw data.

In view of these challenges, in one embodiment, a median filter, such as median filters available for use with MATLAB data analysis software, developed by MathWorks, Inc., can be applied to the actual CTP and RCB images 314, 320 after the background artifacts are removed. Median filters have the advantage of reducing pollution of CTP and RCB by border points not already rejected by the guard bands, providing an elegant solution to an optimal value without modifying the raw data. Applying a median filter to the actual CTP and RCB images (e.g. the camera captured CTP and RCB images) provides a dominant camera-captured CTP color and a dominant camera-captured RCB color. More specifically, the median filter is applied in a line wise direction and then in a column wise direction.

Due to potential variability in lighting conditions under which the digital image is captured, the camera-captured CTP color must be color corrected prior to comparison with the MICC to calibrate the digital image to the MICC/ACC color space. It is noted that since the digital image of the diagnostic instrument captures both the RCB and CTP under the same lighting conditions, the digital image of the RCB reflects the same noise and bias conditions as the CTP. Therefore, the RCB can serve as a calibration reference to color correct the color averaged CTP value.

In one embodiment, a color correction value is determined by identifying a white color sample of the RCB. A color correction factor is determined by identifying any colors, other than white, present in the camera-captured white color sample of the RCB. The correction factor is applied to the camera-captured CTP color using a white balancing algorithm, as is known in the art. For example, white balancing algorithms for use in MATLAB by Jeny Rajan, available at https://sites.google.com/site/jenyrajan/, may be used in connection with the color correction factor. White balancing algorithms are effective for color correcting red, green, blue images, such as the digital image of the diagnostic instrument.

Alternatively, and in a preferred and non-limiting embodiment, a color correction algorithm uses additional reference samples from the RCB to calculate both a black and white correction factor and a color correction factor for the digital image. Inherent to the invented method, the colors of each of the squares in the RCB (Cyan, Magenta, Yellow, Key (black), Gray, White, Red, Green, and Blue) are known under standard lighting (e.g., lighting standard D65) conditions. The color values for the RCB under standard lighting conditions are referred to as the ReferenceRCB (RefRCB) values. These known standard color values are compared to values obtained from the actual RCB image 322, referred to as the camera-captured RCB (CCRCB), acquired according the process described above. Having two data sets, the CCRCB and the RefRCB, it is possible to construct an inverse matrix that transforms the CCRCB into RefRCB. An example of a solution for deriving the inverse matrix and for correcting the color of the CTP based on the derived inverse matrix, includes the following:

1. Correct the image by adjusting the luminance of the squares with the gamma factor $$L_{out} = A \cdot L_{out}^{gamma}$$

This is for B&W luminance, which represents the bulk of the correction.

2. Correct the RGB bias by balancing the three colors with another gamma factor.

$$a_{out} = B \cdot a_{out}^{gamma1}$$

This is for color adjustments, typically a and b and Lab.

3. Use CMY values for validation.

Once the Gamma factors (A, gamma, B, gamma1) are derived, the correction is applied to the dominant camera-captured CTP color to bring the CTP color into the MICC/ACC color space.

Figure 9:
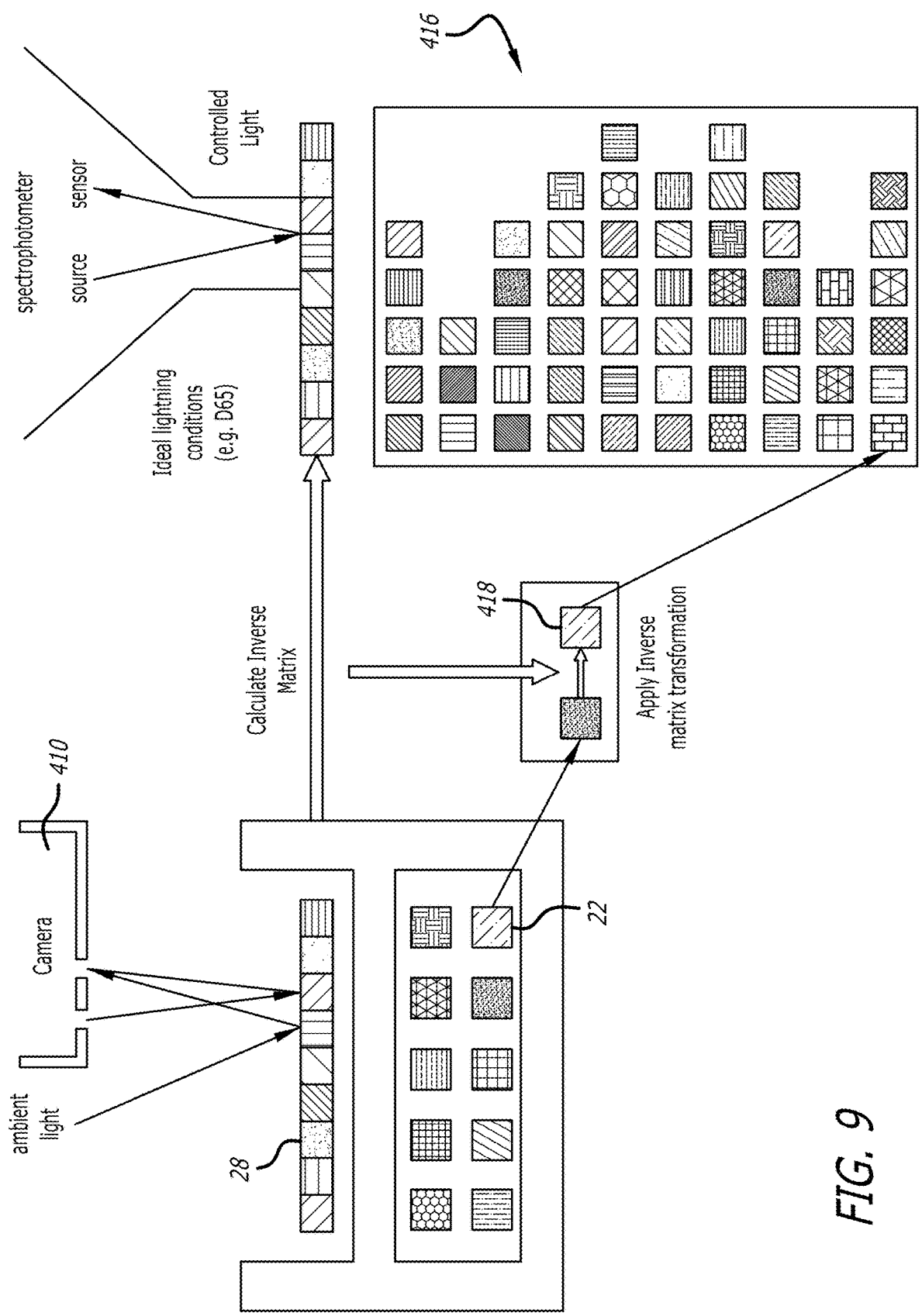
FIG. 9 is a schematic view of the process for color correcting a digital image of the chemical test pads (CTPs).

A schematic representation of the above described color correction process is depicted in FIG. 9. As shown in FIG. 9, the digital image of the diagnostic instrument 10 including the CTP 22 and RCB 28 is obtained using a camera 410 of the portable electronic device under real or unknown lighting conditions. This is the CCRCB. The digital image of the RCB 28 is compared to known color values for the RCB 28 obtained under standard or ideal lighting conditions using a spectrophotometer 412. This image is referred to as the RefRCB. The comparison between the CCRCB and RefRCB is used to create an inverse matrix 414 for mapping the CCRCB onto the RefRCB. The inverse matrix 414 is applied to the camera-captured CTP color to transform the camera captured CTP color into a color in the same color space as the MICC/ACC 416. Once the CTP is transformed to obtain a color corrected CTP color 418, the color corrected CTP can be compared with the appropriate MICC/ACC 416 since both colors are presented in the same color space. In this way, the digital image of the diagnostic instrument is effectively calibrated with the MICC/ACC 416, even though the digital image was obtained under real or unknown lighting conditions.

Compare CTP to their Corresponding MICC/ACC

The MICC/ACC for a number of different types of CTP arrangements may be stored on computer-readable media included on or associated with the portable electronic device. With reference to FIG. 4, when the method validates the UID at step 216, it also selects the corresponding MICC/ACC to interpret the paddle. More specifically, the validation process uses the identification information included on the UID of the diagnostic instrument being tested to select the correct MICC/ACC to interpret results of a specific test. The validation process effectively prevents a user from using the wrong diagnostic instrument or incorrect MICC/ACC, even when several families of diagnostic instrument products have a similar appearance or CTP arrangement. The color corrected CTP color is compared with color values from the corresponding MICC/ACC to determine the analyte concentration of the sample solution. The measured color is compared to the MICC/ACC values by an interpolation process.

Figure 10:
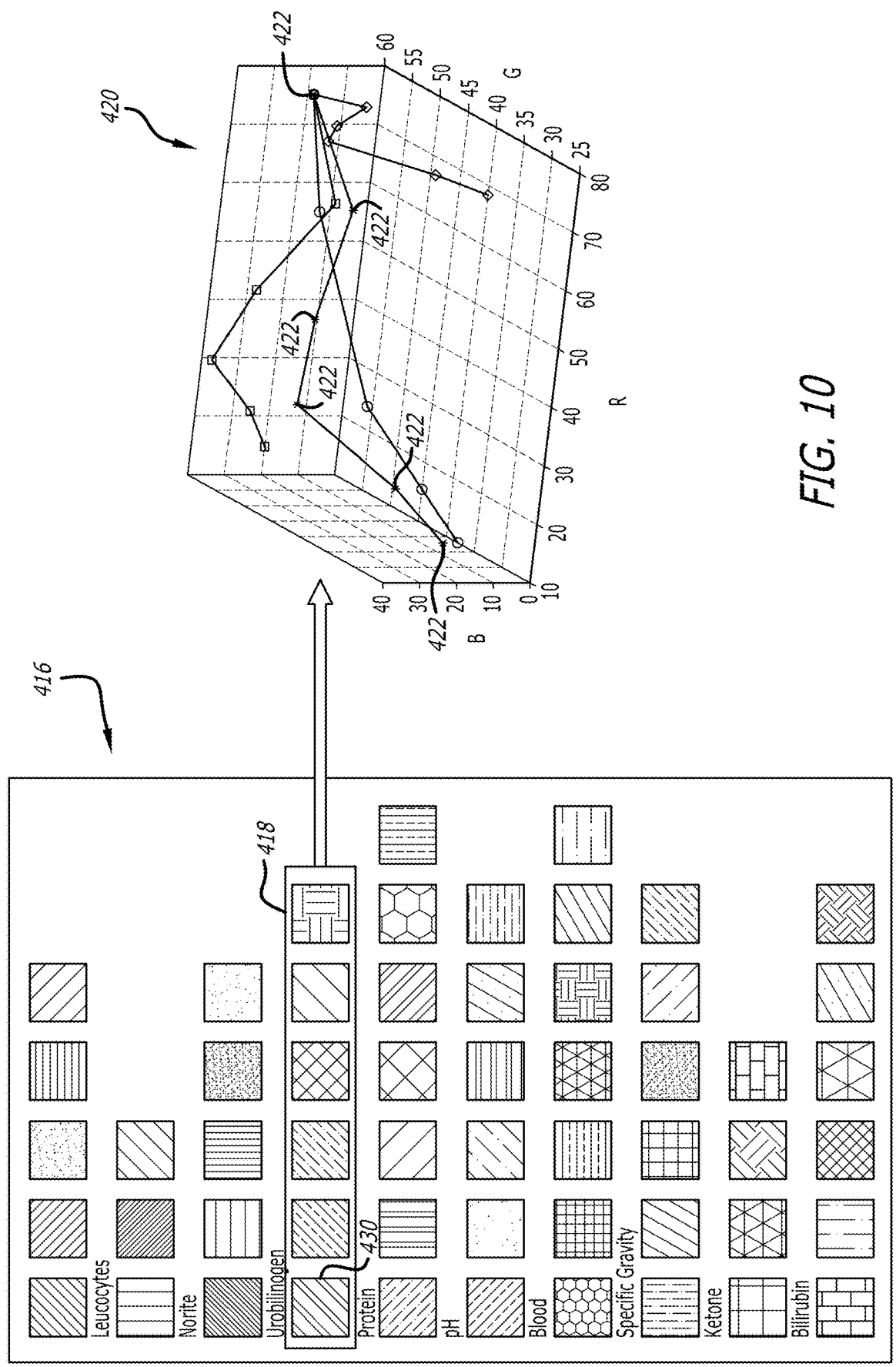
FIG. 10 is a schematic representation indicating that color samples from a Manufacturing Interpretation Color Chart are mapped in the Red-Green-Blue (RGB) color space.
Figure 11:
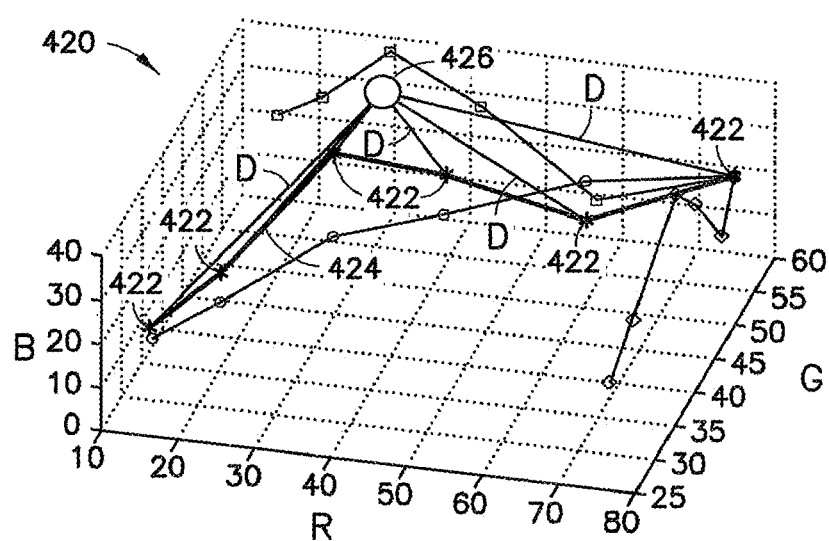
FIG. 11 is a schematic view of the RGB color space of FIG. 10, including the color samples from the MICC and a corrected test medium color.

Interpolation of test results using the MICC/ACC can be performed in at least two ways. With reference to FIGS. 10 and 11, the first and simplest method, which is employed in imaging processes employed in the prior art, is assessment of the distance in the color space between the color corrected CTP color and MICC/ACC values. A schematic drawing depicting such interpolation is depicted in FIGS. 10 and 11. As shown in FIG. 10, the MICC/ACC 416 for a particular CTP (e.g., a set 418 of a plurality of color samples 430 or color values representing the color change for various analyte concentrations of a given analyte) is represented in the RGB color space 420 as a series of discrete points 422. The points 422 in the color space correspond to the set 418 of color samples 430 of the MICC/ACC 416 for a given analyte.

As shown in FIG. 10, the discrete points 422 are connected together to form a solid color trajectory line 424. Other color trajectory lines are shown in FIG. 10 with different points. The other color trajectory lines represent other sets of color samples 430 and the MICC/ACC 416 for CTPs with different analytes.

With reference to FIG. 11, the color corrected CTP color 426 is also included in the color space 420. The method calculates the distance D between the color corrected CTP color 426 and each of the discrete points 422. The nearest discrete point 422 is thereby identified. The test result for the CTP color is reported as the analyte concentration of the closet discrete point.

Figure 12A:
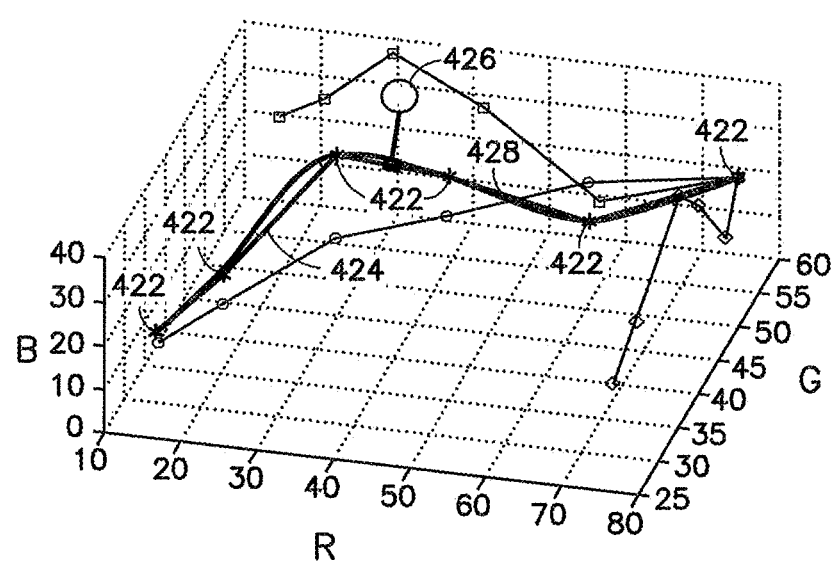
FIG. 12A is a schematic view of the RGB color space including a color trajectory derived from the MICC color samples and a corrected test medium color.
Figure 12B:
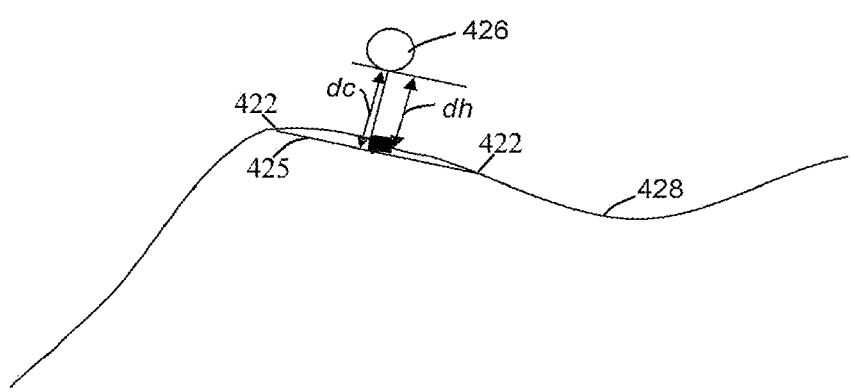
FIG. 12B is a magnified schematic view of the color trajectory of FIG. 12A.

With reference to FIGS. 12A and 12B, a second preferred method, introduces an additional metric by using the shortest distance dh between the color corrected CTP color 426 and an interpolated color trajectory 428 derived from the discrete points 422. The distance dh may be used in two simultaneous ways. First, a color trajectory function may be derived by, applying polynomial interpolation. The shortest perpendicular distance dh between the color corrected. CTP color 426 and the interpolated color trajectory 428 is used to calculate the predicted concentration. Secondly, if the length dh of the perpendicular to the interpolated color trajectory 428 is larger than a predetermined value, then the measurement is rejected as suspect. Conversely, if dh is less than a given predetermined value, the measurement may be assumed to be trustworthy.

Referring now to FIG. 12B, the determination of concentration may be further refined by proportional interpolation between the two closest discrete points 422 to the color corrected CTP 426 to further improve quantitative accuracy, using known algorithms. In an alternative embodiment, the perpendicular distance de between the color corrected CTP color 426 and a trajectory line 425 connecting the discrete points 422, defined as the chord 425 between the discrete points 422, also yields a valuable and simplified method for calculating concentration from the measured color.

In either case, the color corrected portion of the digital image including the CTP is proportionally mapped on to the precisely interpolated polynomial, or chordal, fit in the chosen color space (e.g., the red-green-blue (RGB, International Commission on Illumination (CIE) XYZ, or the International Color Consortium (ICC) device independent color space (L*a*b color space)) color space). Although the discussion herein often refers to the RGB color space, it will be appreciated by those well versed in the art that any color space may be used (e.g., CMYK, CIE, Pantone, Munsell, etc.).

Beneficially above method is quite tolerant of nonlinearities, and does not require a unitary relationship with any human visual properties, making its numerical value and interpretation independent of the color vision of the observer, ambient lighting when the digital image was taken, residual metamerism, or indeed most commonly encountered errors, for which calibration and compensation did not formerly exist.

Once a plurality of analyte concentrations are calculated, the test results may be provided to a user. Additionally, the complete set of test results may be interpreted in combination as a medically-coherent set, to more specifically determine a patient condition.

Compare a CTP to an Experimentally Built MICC/ACC in Single Lighting Lab Conditions MICC charts provided by manufacturers are printed for color recognition through the human eye in controlled lighting environments. For example, the single lighting lab condition may be at an luminance of 1600 lux. Because the color recognition is through the human eye and under a single lab lighting condition, these charts are not well suited to machine recognition. Additionally, the printing process reduces significantly their gamut and the perceived result depends also on the paper quality, paper gloss, ink gloss as well as the light used to observe the scene.

New MICC/ACC charts are established experimentally under controlled lighting conditions, such as luminances of 60 lux, 160 lux, 260 lux, 550 lux, and 1600 lux, using a color camera. These charts are built on lab-based chemical experiments. Chemical test pads, such as CTPs 22 of the test strip 14 shown in FIG. 1 for example, are dipped for a constant time into known control solutions triggering those CTPs to develop colors during a controlled time period. The pictures of these CTPs are then captured by a camera, stored in an experimental MICC/ACC chart database and used in the color recognition of exposed CTPs with unknown concentrations. These new MICC/ACC absolute values provide measurement points directly in red-green-blue (RGB) colors for each CTP titration. Together these points form a trajectory that the CTPs follow in the color space when covering their nominal range of titration for an analyte. Different colors of a given CTP representing different titrations or concentrations of an analyte in an MICC/ACC chart may be used for comparison to determine an unknown concentration in a biological sample.

Figure 20:
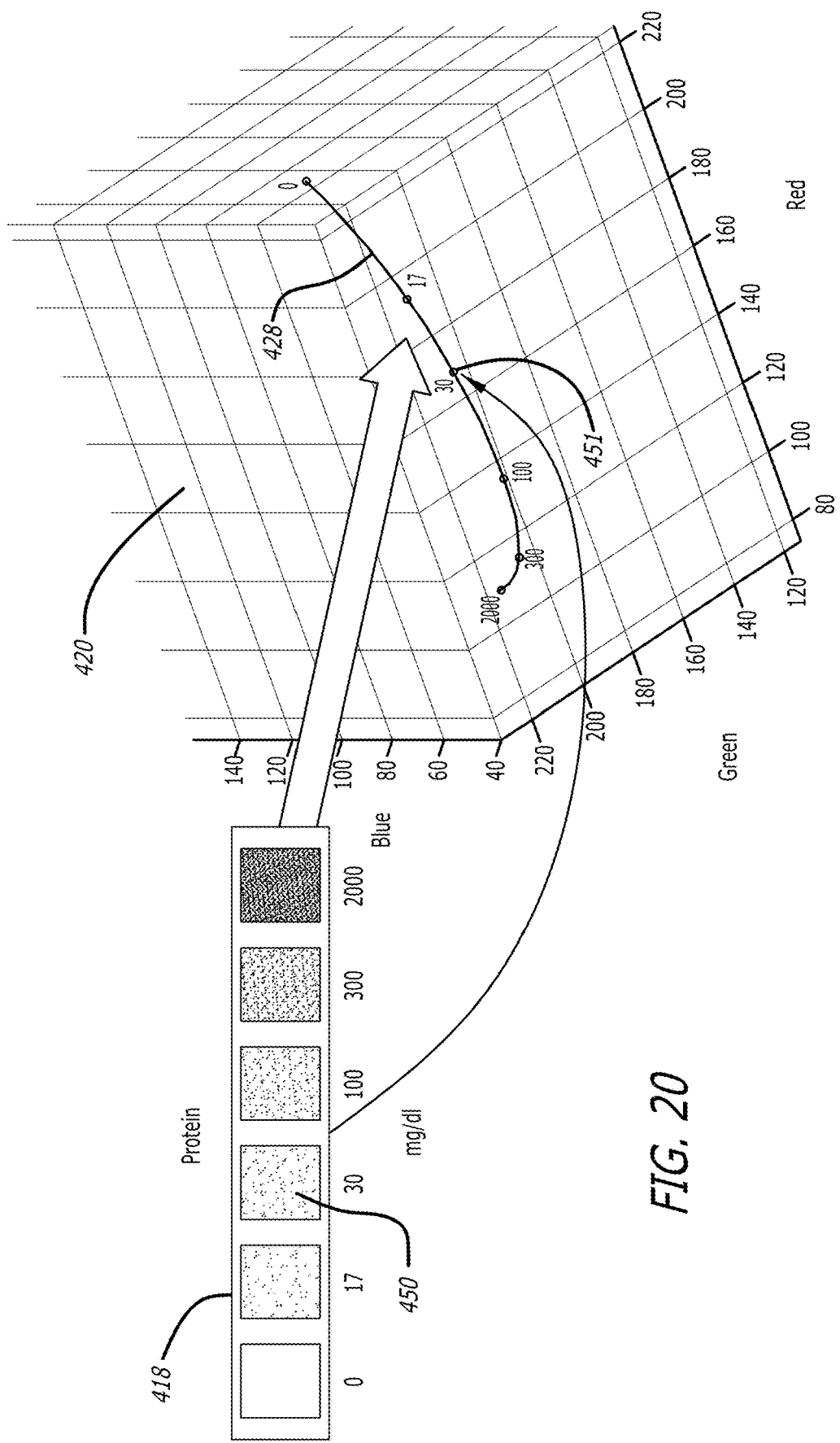
FIG. 20 is a schematic view of a method for constructing an absolute color curve—(ACC).
Figure 21:
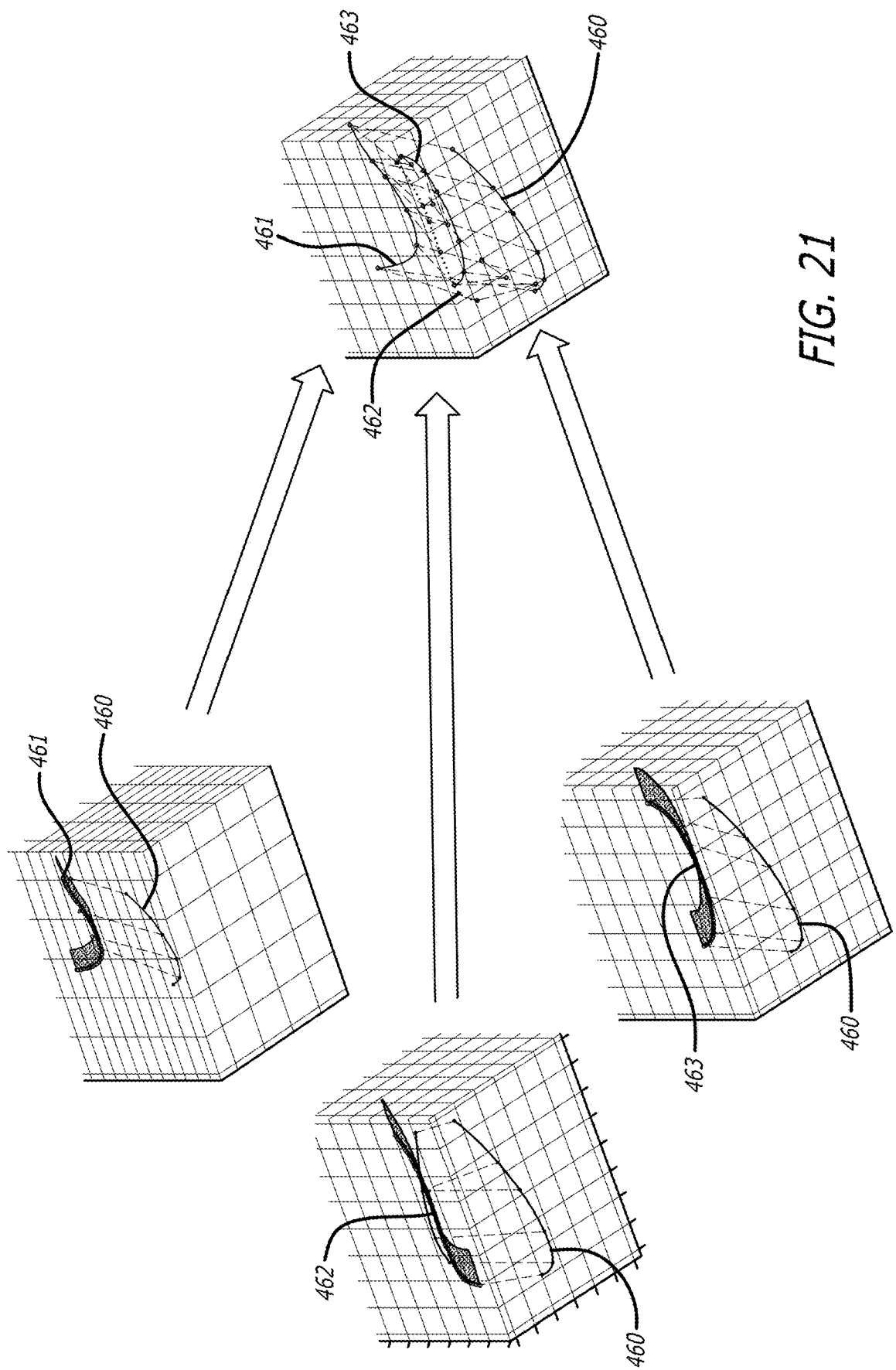
FIG. 21 is a schematic view of a method for shifting absolute color curves according to lighting conditions and combining them with the original absolute color curve into a set of color trajectories used for recognition under any lighting condition.

FIG. 20 illustrates an example of an experimentally built MICC/ACC chart 418 of a plurality of color samples for a protein with titrations from left to right of 0, 17, 30, 100, 300, 2000 milligrams per deciliter (mg/dl). The plurality of color samples provide corresponding points (from right to left) in the RGB color space 420 representing protein titration levels (PRO) under one of the known controlled lighting conditions (e.g., 60 lux, 160 lux, 260 lux, 550 lux, or 1600 lux). For example, a color sample 450 of the CTP for the titration of 30 mg/dl is reported in the RGB space 420 as point 451 (PRO 30). The collection of protein titrations of 0, 17, 30, 100, 300, 2000 mg/dl generates a plurality of trajectory points (PRO 0, PRO 17, PRO 30, PRO 100, PRO 300, PRO 2000) in the RGB space 420. The trajectory points are approximated by a polynomial interpolation to generate a continuous analytical function mapping trajectory 428, referred to as a measured color trajectory 428, under one of the known controlled lighting conditions (e.g., 60 lux, 160 lux, 260 lux, 550 lux, or 1600 lux).

Several noise reduction techniques known in the art can be used to increase the precision of such trajectories, as well as to estimate a degree of confidence in the trajectory 428. Experiments have been reproduced several dozen times to statistically evaluate their precision through their average and variance, and to reduce their noise to a level compatible with the color interpretation application of the CTP. The noise is estimated for each point of the continuous trajectory such that it can vary from point to point along the color trajectory 428. The estimated noise for each point on the trajectory can be represented as a generalized tube of confidence T centered around the trajectory 428.

When working in recognition mode, comparing a captured color corrected RGB color of a CTP with unknown titration to the continuous trajectory 428 for one of the known controlled lighting conditions, the method calculates the shortest Euclidian distance dh in the RGB color space between the trajectory 428 and the color corrected CTP measurement with unknown titration. The point on the trajectory 428 at the shortest Euclidian distance dh from the point of the color corrected CTP measurement, represents the titration measurement for a given analyte associated with the CTP.

In accordance with an embodiment, a simple method to evaluate the quality of the titration measurement is implemented. It is expected that the shortest Euclidian distance dh between the measured point and the trajectory 428 of known controlled lighting conditions (e.g., 60 lux, 160 lux, 260 lux, 550 lux, or 1600 lux) may not be zero due to noise. The noise adds variance to the captured color. As mentioned previously, experiments have provided an estimated noise for each point on the trajectory that can be represented as a generalized tube of confidence T centered around the trajectory 428. The radius and diameter of the tube of confidence T varies along the measured points and the color trajectory curve 428. If the shortest Euclidian distance dh is within the generalized tube of confidence T, the measurement is accepted because it is within a statistically acceptable variance around the color trajectory. If the shortest Euclidian distance dh is outside the tube of confidence T, it is outside the acceptable variance and is rejected.

Figure 22A:
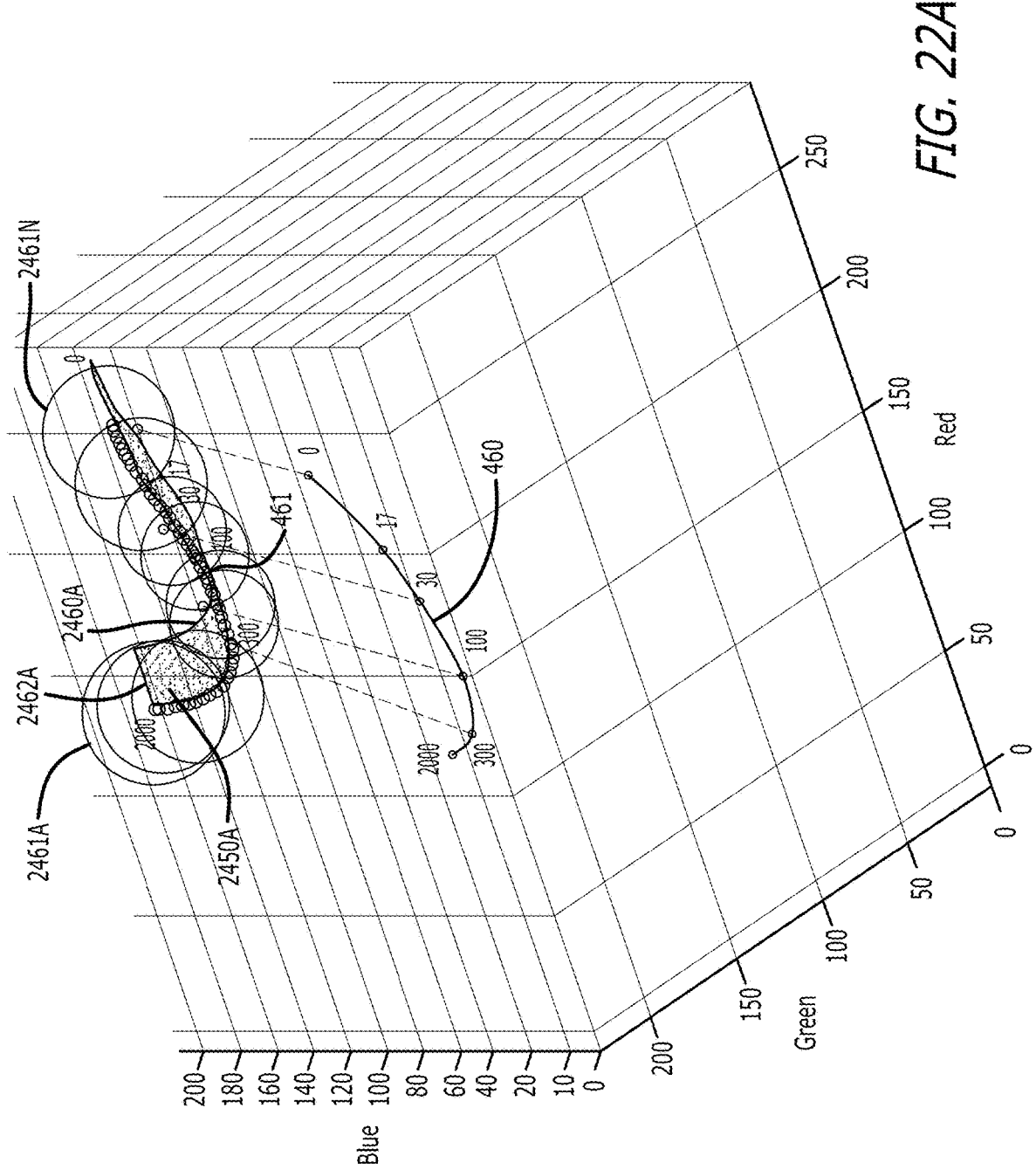
FIGS. 22A-22D are enlarged views of portions of FIG. 21.

Referring now to FIG. 22A, it is desirable to simplify the determination if the Euclidian distance dh is within or outside the tube of confidence T. The tube of confidence T can be represented by a series of spheres 2461A-2461N with center points along the measured points associated with the color trajectory curve 428. Each of the spheres 2461A-2461N has a radius at a given point equal to the radius of the tube of confidence tube that represents the confidence level at that given point. The radius of the tube of confidence at a given point along the color trajectory curve can be determined by projecting radius of the tube of confidence into a vector in the red dimension of RGB color space (tube radius, 0, 0) from the given point. For example, the sphere 2461A has a single color vector 2462A in the red dimension (tube radius, 0, 0) only from the point PRO 2000.

The tube radius at the point PRO 2000 represents the confidence of a measurement that projects its Euclidean distance near the point PRO 2000. Accordingly, the tube radius from the point on the curve may be compared with the shortest Euclidian distance dh to determine if a measured point is within or outside the tube of confidence.

The series of single color vectors in the red dimension for each of the measured points along the color trajectory curve may be graphically represented in FIG. 22A by a ribbon 2450A adjacent the color trajectory curve. If the ribbon 2450A were to be spun around the color trajectory curve 461, the tube of confidence T would be formed. The values for radius along the color trajectory can be extrapolated to form a confidence curve 2460A at the edge of the ribbon 2450A.

The radius of the tube of confidence can be used to define a diameter (twice the radius) around the color trajectory curve 461 under which measurements can be accepted and rejected. Measurements outside the diameter defined by the confidence curve 2460A and the ribbon 2450A are outside the acceptable variance and are rejected. Measurements on and within the diameter defined by confidence curve 2460A and the ribbon 2450A are within the acceptable variance and are accepted measurements. If the measurement is accepted, the titration can then be determined.

With reference to FIG. 20, the general tube of confidence can be applied to a single measured color trajectory 428. However, color measurements of a CTP are often captured under different lighting conditions. Accordingly, multiple measured color trajectories of an MICC/ACC may be captured under a plurality of known controlled lighting conditions (e.g., 60 lux, 160 lux, 260 lux, 550 lux, and 1600 lux). A tube of confidence T can be applied to each of the known controlled lighting conditions. In this manner, color measurements of a CTP can be captured under unknown lighting conditions and the titration of an analyte can determined by the shortest Euclidian distance dh to a trajectory within the tube of confidence for each of the measured color trajectories.

Compare a CTP to MICC/ACC in Multiple Lighting Conditions

Embodiments are destined to be used in different lighting conditions, such as may be found at a user's home or a doctor's office. Typical light conditions can range from dim lighting (about 50 lux in a living room) to office lighting (about 500 lux) through to studio lighting (around 1000 lux) or laboratory lighting (around 1600 lux). All other things being equal, the color of a CTP changes somewhat in response to different lighting conditions.

The simplest method to overcome these color variations of a CTP due to the various lighting conditions is to repeat all tests performed for an original trajectory 460 for each different lighting condition. That is, multiple measured color trajectories of an MICC/ACC may be captured under a plurality of known controlled lighting conditions (e.g., 60 lux, 160 lux, 260 lux, 550 lux, and 1600 lux). This method of compensating for color variations under different lighting conditions requires many tests. Accordingly, capturing measurements for multiple measured color trajectories of an MICC/ACC under a plurality of different lighting conditions (e.g., 60 lux, 160 lux, 260 lux, 550 lux, and 1600 lux) can be time consuming and expensive.

Capturing color points for multiple measured color trajectories of an MICC/ACC under a plurality of different lighting conditions may be automated to reduce time and expense. However, a faster and cheaper alternate method to account for color variations due to the various lighting conditions is to shift an original measured color trajectory under one known lighting condition (e.g., a luminance of 1600 lux) into shifted color trajectories representing other lighting conditions (e.g., 60 lux, 160 lux, 260 lux, and 550 lux).

Referring now to FIG. 21 and FIGS. 22A-22D, the original color trajectory 460 of an analyte measured under lab lighting conditions (e.g., a luminance of 1600 lux) may be shifted into shifted color trajectories according to measurements made under different lighting conditions, such as dim lighting (about 50 or 60 lux in a living room); office lighting (about 500 or 550 lux); studio lighting (around 1000 lux), and other lighting conditions with various luminance values. The shifts to the original color trajectory for an analyte to form a shifted color trajectory may or may not be linear depending on the specific lighting conditions and light spectrum. Accordingly, the shape of a shifted color trajectory for a different light condition may not linearly match the shape of the original measured color trajectory.

A pair of measurements may be used to form a shifted color trajectory. In one embodiment, a measurement of the trajectory shift under new lighting conditions is performed and the original measured color trajectory 460 is mapped to a shifted color trajectory by performing a polynomial interpolation between them.

FIGS. 21 and 22A-22C illustrate three resulting shifted trajectories 461, 462, 463, from the original measured color trajectory 460 to reflect the lighting changes under known different lighting conditions (e.g., 60 lux, 160 lux, 260 lux, 550 lux). A fourth shifted trajectory 464 is shown in FIG. 22D from the original measured color trajectory 460 to reflect the lighting change under another differing light condition.

Figure 22B:
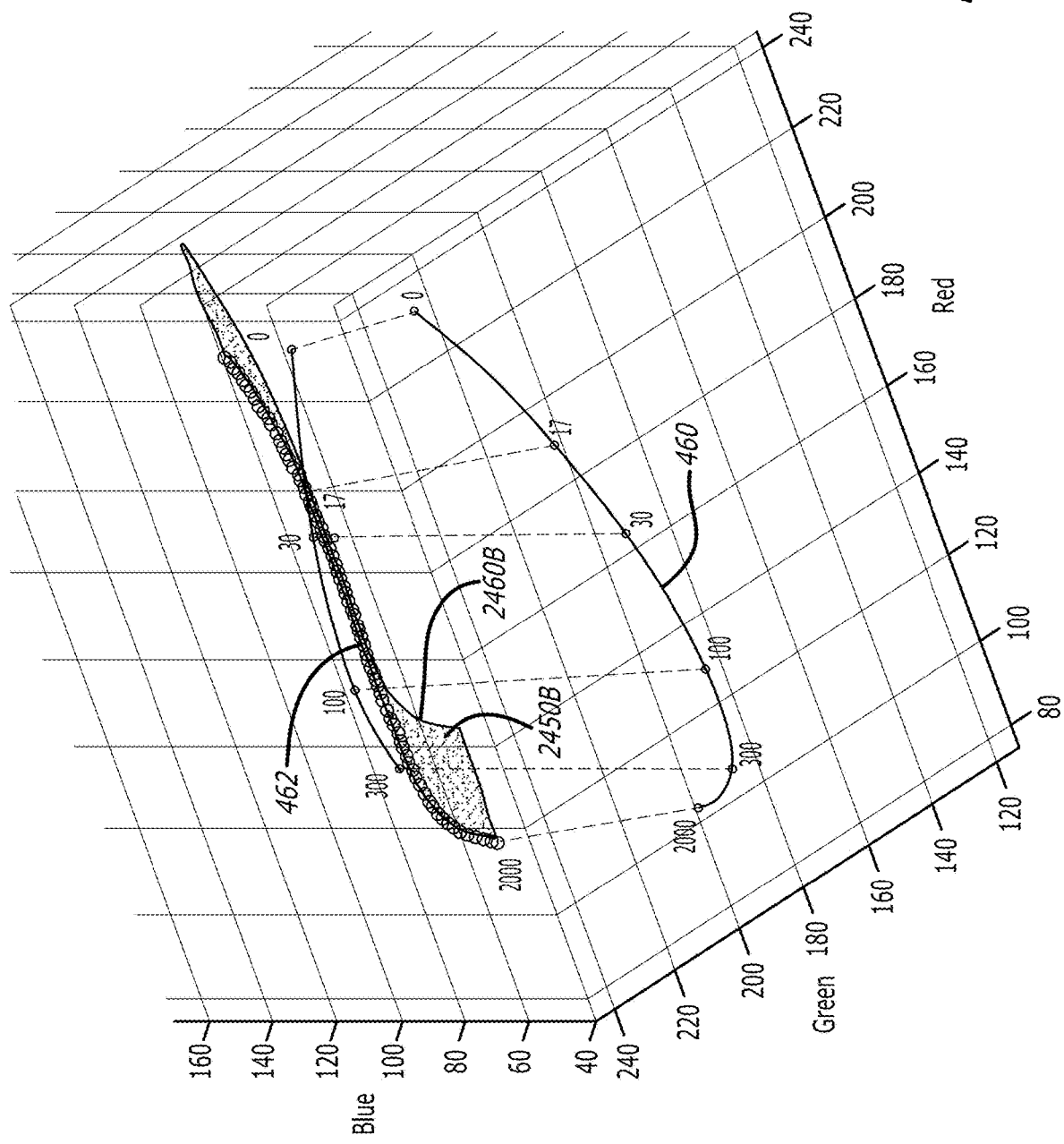
Figure 22C:
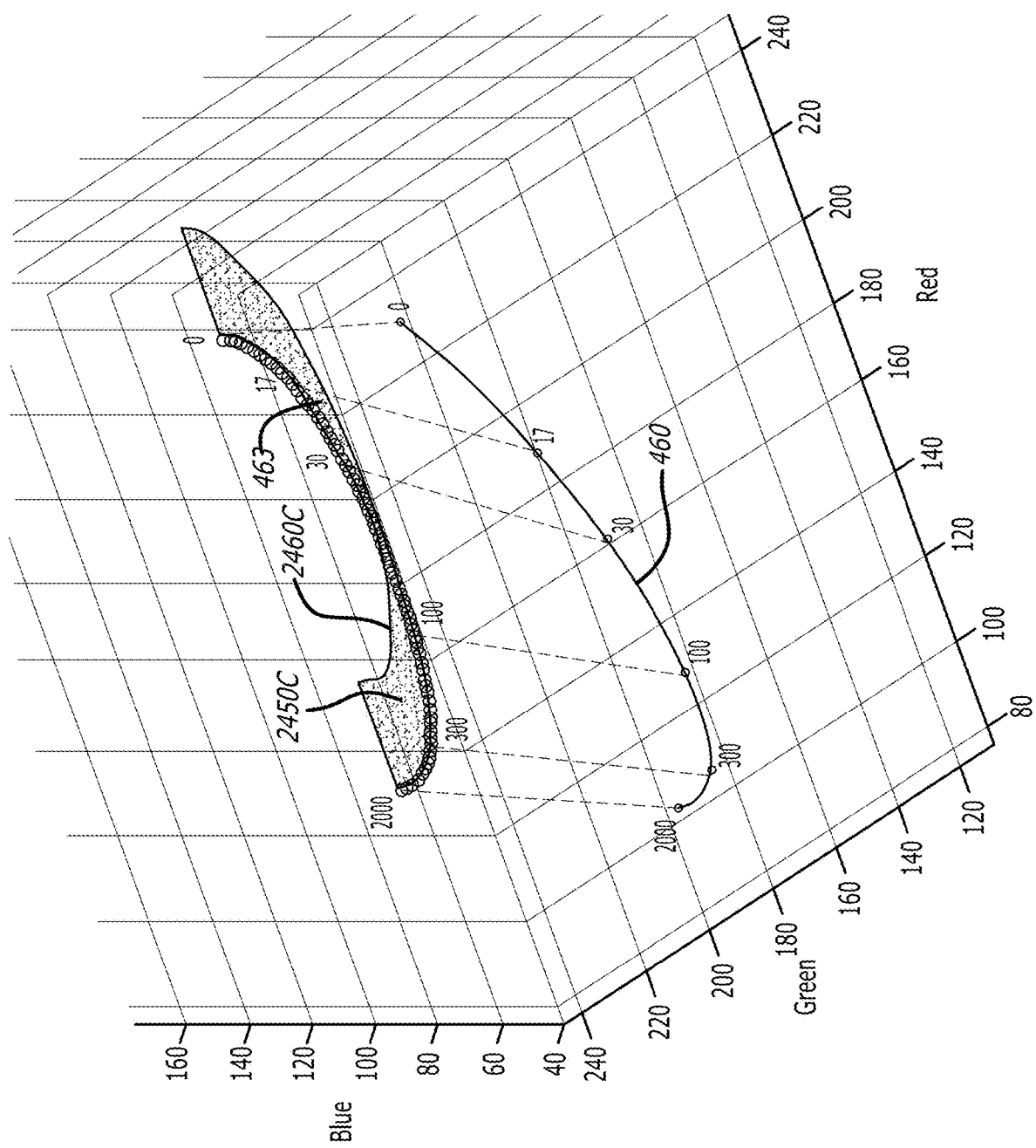
Figure 22D:
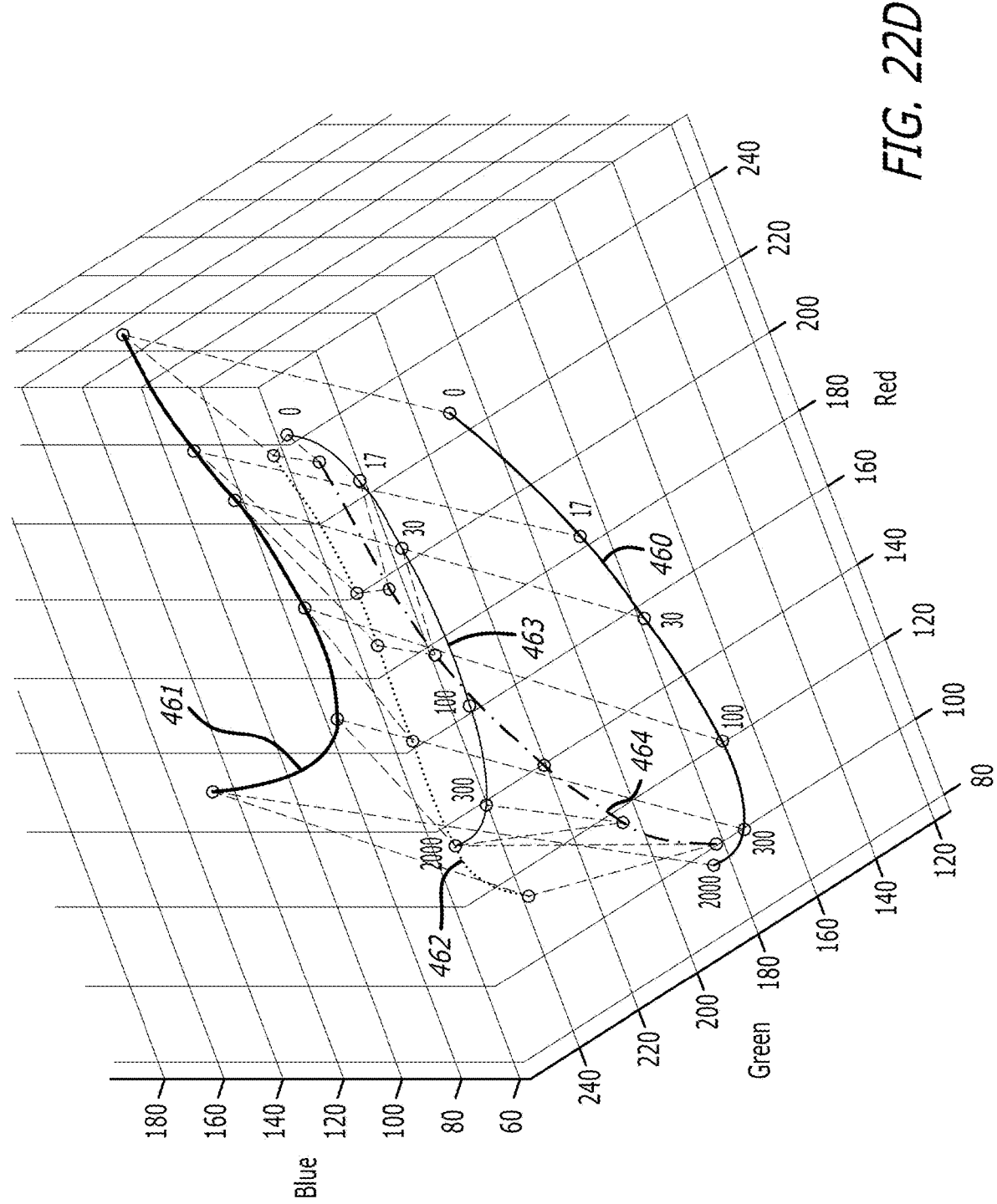

With reference to FIG. 22D, the original measured color trajectory 460 and the resulting shifted color trajectories 461, 462, 463, and 464 are gathered as a set of color trajectories for the MICC/ACC under different lighting conditions. The set of color trajectories for the MICC/ACC under different lighting conditions may then be used for color recognition of the measured color of a CTP for a given analyte and titration of a biological sample.

Test Results with Multiple Trajectories

In FIG. 22D, a different tube of confidence T can be associated with each of the original measured color trajectory 460 and the differing shifted color trajectories 461-464 that form the set of color trajectories for the MICC/ACC under the respective different lighting conditions.

A tube of confidence T for the shifted color trajectory 461 is described with reference to FIG. 22A. Tubes of confidence T for each of shifted color trajectories 462 and 463 are described with reference to FIGS. 22B and 22C.

FIG. 22B shows a ribbon 2450B of confidence that represent the radius of the tube of confidence T along points of the shifted color trajectory 462 associated with a different controlled lighting conditions (e.g., 60, 160, 260, 550, 1600 lux). The values for radius along the color trajectory 462 can extrapolated to form confidence curve 2460B at the edge of each of the ribbon 2450B.

FIG. 22C shows a ribbon 2450C of confidence that represent the radius of the tube of confidence T along points of the shifted color trajectory 463 associated with a different controlled lighting condition (e.g., 60, 160, 260, 550, 1600 lux). The values for radius along the color trajectory 463 can extrapolated to form confidence curve 2460C at the edge of the ribbon 2450C. The set of color trajectories for the MICC/ACC of a given analyte under different lighting conditions can be plotted together in one chart.

Additional shifted color trajectories for different luminances can be formed from the original measured color trajectory 460, such as the shifted color trajectory 464 shown in FIG. 22D. The resulting shifted color trajectories 461-464 from the original measured color trajectory 460 and the original measured color trajectory 460 form a set of color trajectories for the MICC/ACC of a given analyte under different lighting conditions. The set of color trajectories for the MICC/ACC under different lighting conditions are used for comparison and color recognition of the color of a CTP for a given analyte for the respective method steps 2900A-2900B shown in FIGS. 19A-19B. Color measurements of a CTP associated with an analyte can be captured under unknown lighting conditions providing measured points to determine Euclidian distances dh to color trajectories in the set of color trajectories for the MICC/ACC. Titration of the analyte can be determined by the shortest Euclidian distance dh being within the associated tube of confidence to one of the color trajectories of the set.

Test Results and Titrations of CTP

Figure 13:
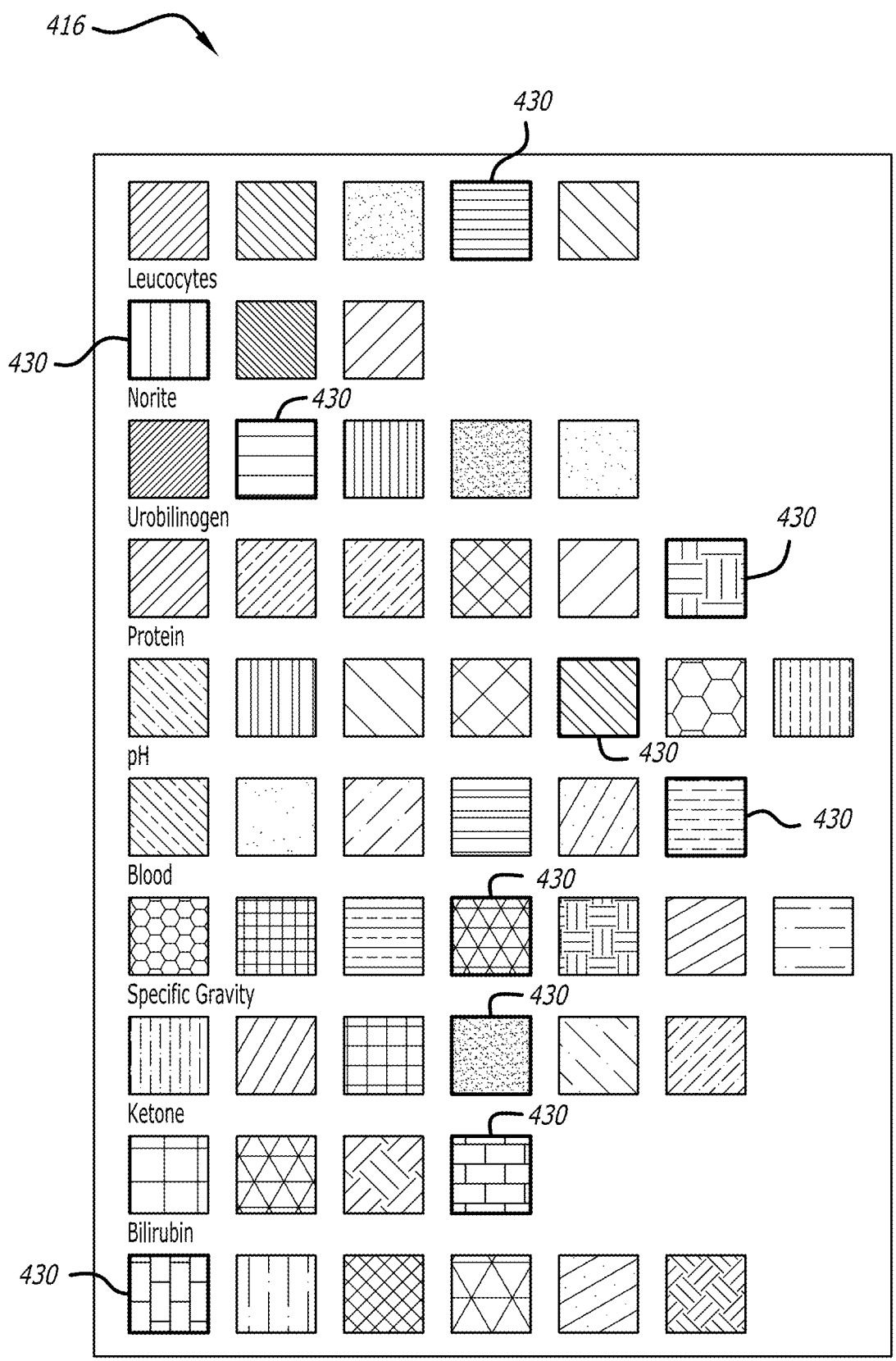
FIG. 13 is a photographic representation of a Manufacturing Interpretation Color Chart with test results identified.

The titration or concentration of an analyte can be determined from the shortest Euclidian distance dh for a measured point within the tube of confidence for a color trajectory of an associated lighting condition. Test results are presented to a user by a visual display connected to or associated with the portable electronic device. A simple way to visualize test results is to present the user with an image of the MICC and draw a border around the closest MICC/ACC color samples. A possible visual depiction of an MICC/ACC 416 showing selected color samples 430, corresponding to the identified test results, is depicted in FIG. 13.

Another way to visualize test results is to print the analyte being tested for and the concentration or titration (e.g. normal, positive, very positive, etc.) in a list or table. The list or table can be presented on the visual display of the device, as shown below in Table 1. The correspondence between these the titrations and the colors read by the algorithm is encoded in a look-up table linking the MICC/ACC to the titrations. Typical values provided are negative (−), trace, small (+), moderate (++), and large (+++).

TABLE 1

| | |
|---|---|
| Leukocytes | Moderate |
| Nitrate | Negative |
| Uro-bilinogen | 1 |
| ... | |

Interpretation of the Result

The test results may be further analyzed to provide the user with information about a possible patient condition. In a simple form, the interpretation may include displaying additional facts about the patient condition and possible treatment options. In further embodiments, the method may consider results of two or more separate tests to provide additional information about a patient condition. For example, an indication that the patient has both high leucocytes levels and high nitrites suggests a urinary tract infection (UTI).

In cases where this interpretation might lead to ambiguity, the software may engage in a user dialogue by asking additional contextual questions to the user in order to resolve ambiguities and provide an approximate interpretation in accordance with the medical state of the art. These additional questions are typically implemented as a decision tree, a method well known in the state of the art. For example if the diagnostic instrument 10 identifies a high level of bilirubin, the decision tree function of the software may ask the user for additional information about medications being taken to detect whether the user is experiencing an allergic reaction to a particular medication. Exemplary decision trees for use with the diagnostic instrument are depicted in FIGS. 14 and 15.

Secure Embodiment for Verification of Unused Diagnostic Instrument

In a further non-limiting embodiment of the invented method, the diagnostic instrument may be examined prior to use to ensure that it is undamaged and suitable for use. More specifically, storage, conditioning, transport and the exposure of the diagnostic instrument to contaminants like air, could damage the diagnostic instrument, making it unreliable in use. It is noted that exposure to containments may render the diagnostic instrument unsuitable for use even if the diagnostic instrument has not yet reached its anticipated expiration date. Accordingly, steps are needed to ensure that the diagnostic instrument is capable of producing accurate results.

Figure 16:
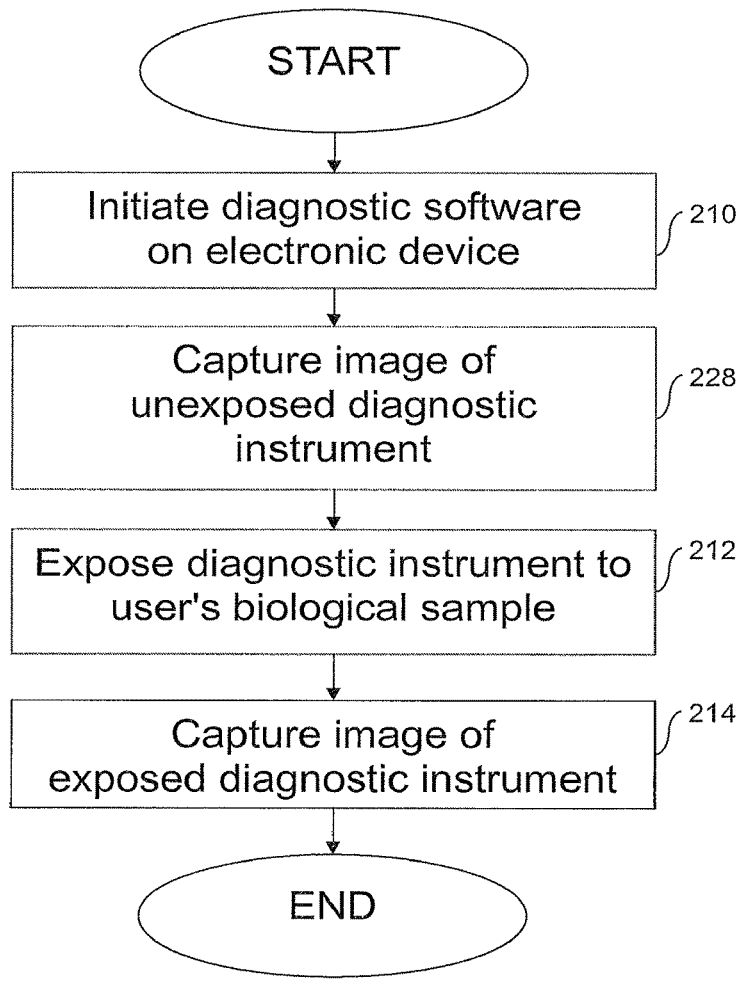
FIG. 16 is a flow chart of an embodiment of a method for capturing an image of a diagnostic instrument.
Figure 17:
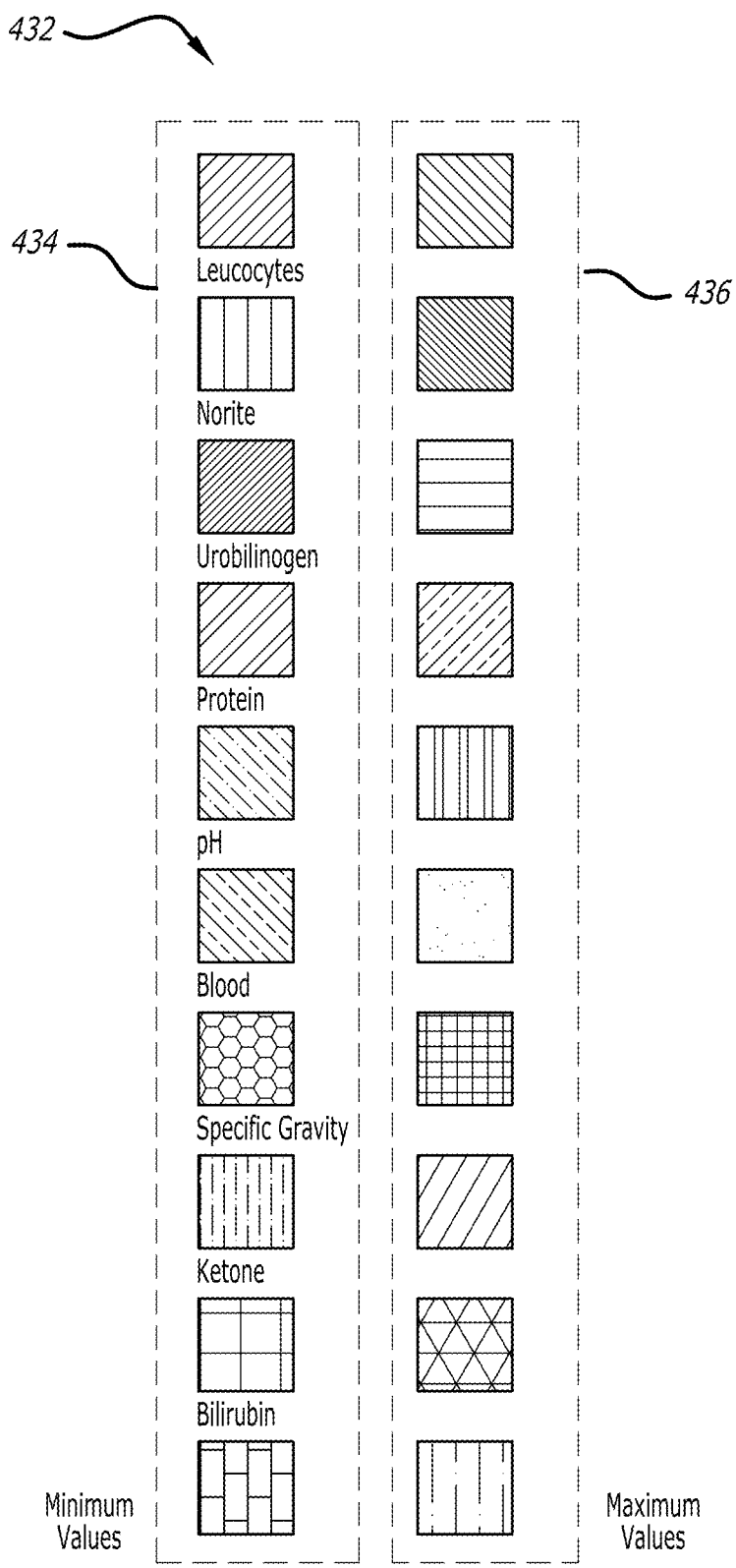
FIG. 17 is a schematic view of a table depicting minimum and maximum color change values for a plurality of chemical test pads, for use in verification of a diagnostic instrument.

As shown in the exemplary embodiment of FIG. 16, in this embodiment, the user captures an image of the diagnostic instrument prior to exposing the diagnostic instrument to the biological sample 228. The other steps are equivalent to the method for capturing a digital image depicted in FIG. 3. The step of capturing the image of the unexposed diagnostic instrument prior to exposing the instrument to the fluid sample is used to verify that the initial (e.g. unused) colors of the CTP, prior to coming into contact with the fluid sample, are within a normal range. More specifically, the appearance of the unused CTP is compared to expected original values by using the algorithms for color comparison described above, in connection with comparing the color-corrected CTP color to the MICC/ACC. However, rather than comparing the color corrected CTP colors to the MICC/ACC, the color corrected CTP values are compared against a Security Table built during the risk and quality management process for the diagnostic instrument. An exemplary Security Table 432 is depicted in FIG. 17. The Table 432 includes a minimum possible subset 434 of colors for each unused CTP. If the color corrected CTP color for the unused CTP differs from the color samples of the table 432 by more than a predetermined amount, the diagnostic instrument is rejected as defective. More specifically, the Security Table defines the tolerances of acceptable unexposed diagnostic instrument colors. Any deviation from the expected tolerance is rejected. Notice also that table 432 reflects colorimetric values for dry samples, which might appear lighter color than the wet values processed with exposed samples and reported in the MICC/ACC.

Similarly, after the diagnostic instrument is exposed to the fluid sample and before performing additional image analysis on the diagnostic instrument, a digital image of the diagnostic instrument could be compared against a set of colors 436 corresponding to the maximum possible CTP color change. The method of comparing the color change of the CTP with the maximum color change values is the same as the above described comparison processes. If the color change of the CTP is found to exceed the theoretical maximum possible color change, the results are rejected as invalid. In that case, no further image processing needs be performed and the diagnostic instrument should be discarded as defective.

The above described methods may be implemented on a variety of electronic and computing devices and systems, including portable electronic devices and/or server computers, wherein these computing devices include appropriate processing mechanisms and computer readable media for storing and executing the computer readable instructions, such as programming instructions, code, and the like.

Figure 18:
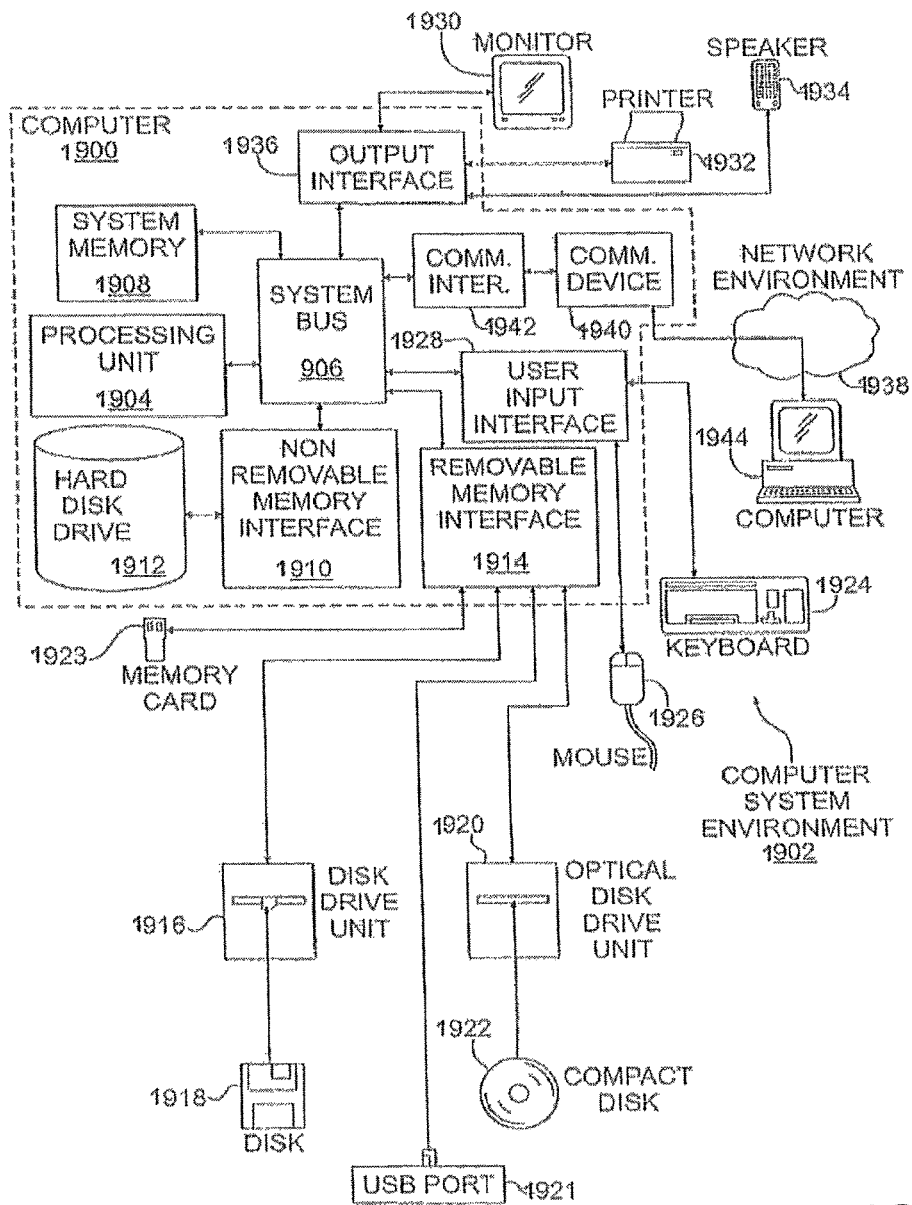
FIG. 18 is a schematic diagram of a computer network infrastructure according to the prior art.

As shown in FIG. 18, personal computers 1900, 1944, in a computing system environment 1902 are provided. This computing system environment 1902 may include, but is not limited to, at least one computer 1900 having certain components for appropriate operation, execution of code, and creation and communication of data. For example, the computer 1900 includes a processing unit 1904 (typically referred to as a central processing unit or CPU) that serves to execute computer based instructions received in the appropriate data form and format. Further, this processing unit 1904 may be in the form of multiple processors executing code in series, in parallel, or in any other manner for appropriate implementation of the computer-based instructions.

In order to facilitate appropriate data communication and processing information between the various components of the computer 1900, a system bus 1906 is utilized. The system bus 1906 may be any of several types of bus structures, including a memory bus or memory controller, a peripheral bus, or a local bus using any of a variety of bus architectures. In particular, the system bus 1906 facilitates data and information communication between the various components (whether internal or external to the computer 1900) through a variety of interfaces, as discussed hereinafter.

The computer 1900 may include a variety of discrete computer-readable media components. For example, this computer-readable media may include any media that can be accessed by the computer 1900, such as volatile media, non-volatile media, removable media, non-removable media, etc. As a further example, this computer-readable media may include computer storage media, such as media implemented in any method or technology for storage of information, such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer 1900. Further, this computer-readable media may include communications media, such as computer-readable instructions, data structures, program modules, or other data in other transport mechanisms and include any information delivery media, wired media (such as a wired network and a direct-wired connection), and wireless media. Computer-readable media may include all machine-readable media with the sole exception of transitory, propagating signals. Of course, combinations of any of the above should also be included within the scope of computer-readable media.

The computer 1900 further includes a system memory 1908 with computer storage media in the form of volatile and non-volatile memory, such as ROM and RAM. A basic input/output system (BIOS) with appropriate computer-based routines assists in transferring information between components within the computer 1900 and is normally stored in ROM. The RAM portion of the system memory 1908 typically contains data and program modules that are immediately accessible to or presently being operated on by processing unit 1904, e.g., an operating system, application programming interfaces, application programs, program modules, program data and other instruction-based computer-readable codes.

With continued reference to FIG. 18, the computer 1900 may also include other removable or non-removable, volatile or non-volatile computer storage media products. For example, the computer 1900 may include a non-removable memory interface 1910 that communicates with and controls a hard disk drive 1912, i.e., a non-removable, non-volatile magnetic medium; and a removable, non-volatile memory interface 1914 that communicates with and controls a magnetic disk drive unit 1916 (which reads from and writes to a removable, non-volatile magnetic disk 1918), an optical disk drive unit 1920 (which reads from and writes to a removable, non-volatile optical disk 1922, such as a CD ROM), a Universal Serial Bus (USB) port 1921 for use in connection with a removable memory card, etc. However, it is envisioned that other removable or non-removable, volatile or nonvolatile computer storage media can be used in the exemplary computing system environment 1900, including, but not limited to, magnetic tape cassettes, DVDs, digital video tape, solid state RAM, solid state ROM, etc. These various removable or non-removable, volatile or non-volatile magnetic media are in communication with the processing unit 1904 and other components of the computer 1900 via the system bus 1906. The drives and their associated computer storage media discussed above and illustrated in FIG. 18 provide storage of operating systems, computer-readable instructions, application programs, data structures, program modules, program data and other instruction-based computer-readable code for the computer 1900 (whether duplicative or not of this information and data in the system memory 1908).

A user may enter commands, information, and data into the computer 1900 through certain attachable or operable input devices, such as a keyboard 1924, a mouse 1926, etc., via a user input interface 1928. Of course, a variety of such input devices may be utilized, e.g., a microphone, a trackball, a joystick, a touchpad, a touch-screen, a scanner, etc., including any arrangement that facilitates the input of data, and information to the computer 1900 from an outside source. As discussed, these and other input devices are often connected to the processing unit 1904 through the user input interface 1928 coupled to the system bus 1906, but may be connected by other interface and bus structures, such as a parallel port, game port, or a universal serial bus (USB). Still further, data and information can be presented or provided to a user in an intelligible form or format through certain output devices, such as a monitor 1930 (to visually display this information and data in electronic form), a printer 1932 (to physically display this information and data in print form), a speaker 1934 (to audibly present this information and data in audible form), etc. All of these devices are in communication with the computer 1900 through an output interface 1936 coupled to the system bus 1906. It is envisioned that any such peripheral output devices be used to provide information and data to the user.

The computer 1900 may operate in a network environment 1938 through the use of a communications device 1940, which is integral to the computer or remote therefrom. This communications device 1940 is operable by and in communication to the other components of the computer 1900 through a communications interface 1942. Using such an arrangement, the computer 1900 may connect with or otherwise communicate with one or more remote computers, such as a remote computer 1944, which may be a personal computer, a server, a router, a network personal computer, a peer device, or other common network nodes, and typically includes many or all of the components described above in connection with the computer 1900. Using appropriate communication devices 1940, e.g., a modem, a network interface or adapter, etc., the computer 1900 may operate within and communication through a local area network (LAN) and a wide area network (WAN), but may also include other networks such as a virtual private network (VPN), an office network, an enterprise network, an intranet, the Internet, the internet cloud, etc. It will be appreciated that the network connections shown are exemplary and other means of establishing a communications link between the computers 1900, 1944 may be used.

As used herein, the computer 1900 includes or is operable to execute appropriate custom-designed or conventional software to perform and implement the processing steps of the method and system, thereby, forming a specialized and particular computing system. Accordingly, the presently-invented method and system may include one or more computers 1900 or similar computing devices having a computer-readable storage medium capable of storing computer-readable program code or instructions that cause the processing unit 1902 to execute, configure or otherwise implement the methods, processes, and transformational data manipulations discussed hereinafter in connection with the embodiments. Still further, the computer 1900 may be in the form of a personal computer, a personal digital assistant, a portable computer, a laptop, a palmtop, a mobile device, a mobile telephone, a tablet PC, a server, or any other type of computing device having the necessary processing hardware to appropriately process data to effectively implement the computer-implemented method and system.

Although the embodiments has been described in detail for the purpose of illustration based on what is currently considered to be the most practical and preferred embodiments, it is to be understood that such detail is solely for that purpose and that the embodiments is not limited to the disclosed embodiments, but, on the contrary, is intended to cover modifications and equivalent arrangements that are within the spirit and scope of the appended claims. For example, it is to be understood that the embodiments contemplate that, to the extent possible, one or more features of any embodiment can be combined with one or more features of any other embodiment. Moreover, although features may be described above as acting in certain combinations and even initially claimed as such, one or more features from a claimed combination may in some cases be excised from the combination, and the claimed combination may be directed to a sub-combination or variations of a sub-combination. Accordingly, the claimed embodiments is limited only by patented claims that follow below.

What is claimed is:

1. A system for performing diagnostic tests of a biological sample, the system comprising:
   a diagnostic instrument including a color reference with a plurality of reference samples of different colors and a plurality of test media with a plurality of reagents, wherein the plurality of reagents are configured to change color in the presence of various levels of a plurality of different analytes in a biological sample; and
   a portable electronic device including a digital camera sensor configured for capturing a digital image of at least a portion of the diagnostic instrument that has been exposed to the biological sample, and a processor, wherein the processor is configured to:
      identify at least one of the reference samples and at least one of the test media in the digital image of the diagnostic instrument;
      determine a dominant camera-captured color of the at least one reference sample and a dominant camera-captured color of the at least one test media;
      estimate lighting conditions under which the digital image is captured;
      correct the dominant camera-captured color of the at least one test media, based on a color correction factor derived at least in part from the dominant camera-captured color of the at least one reference sample, to determine a corrected test media color; and
      determine a test result including an analyte concentration of the biological sample by a comparison of the corrected test media color to a set of possible test media colors corresponding to predetermined analyte concentrations, wherein the set of possible test media colors is responsive to based at least partly on the estimated lighting conditions under which the digital image is captured.

2. The system of claim 1, wherein the plurality of test media are arranged in a plurality of test specific sequences.

3. The system of claim 1, further comprising an identification label associated with the diagnostic instrument, wherein the digital image includes at least a portion of the identification label.

4. The system of claim 3, wherein the processor is further configured to identify the identification label and validate the diagnostic instrument in response to identification information included on or associated with the identification label.

5. The system of claim 1, wherein the portable electronic device further comprises a data transmitter to transmit at least a portion of the test result to an external source.

6. The system of claim 1, wherein the portable electronic device further comprises a visual display device for displaying instructions for using the system or for displaying the test result.

7. A portable electronic device for analyzing a digital image of a diagnostic instrument, the portable electronic device comprising:
   at least one processor;
   at least one display device coupled in communication with the at least one processor;
   at least one camera sensor coupled in communication with the at least one processor; and
   at least one computer-readable medium coupled in communication with the at least one processor comprising program instructions that, when executed by the at least one processor, cause the portable electronic device to:
   capture a digital image of at least a portion of the diagnostic instrument, which has been exposed to a biological sample, with the at least one camera sensor, the diagnostic instrument comprising at least one color reference comprising a plurality of reference samples of different colors and at least one test medium containing a reagent, which changes color in the presence of particular analytes in the biological sample;
   identify at least one of the reference samples for the at least one test medium in the diagnostic instrument;
   determine a dominant camera-captured color of the at least one reference sample and a dominant camera-captured color of the at least one test medium;
   estimate lighting conditions under which the digital image is captured;
   correct the dominant camera-captured color of the at least one test medium, based on a color correction factor derived at least in part from the dominant camera-captured color of the at least one reference sample, to determine a corrected test medium color; and
   determine a test result including an analyte concentration of the biological sample by a comparison of the corrected test medium color to a set of possible test medium colors corresponding to predetermined analyte concentrations, wherein the set of possible test medium colors is based at least partly on the estimated lighting conditions under which the digital image is captured.

8. The portable electronic device of claim 7, wherein the program instructions further cause the portable electronic device to display use instructions on the at least one display device, and wherein the use instructions explain to a user at least how to expose the diagnostic instrument to the biological sample or how to capture the digital image of the diagnostic instrument.

9. The portable electronic device of claim 8, wherein the use instructions are displayed in conjunction with a video image of the diagnostic instrument.

10. The portable electronic device of claim 7, further comprising a timer and wherein the program instructions further cause the portable electronic device to:
   instruct a user to expose the diagnostic instrument to the biological sample;
   measure a predetermined exposure time with the timer; and
   instruct the user to capture the digital image with the at least one camera sensor after the predetermined exposure time has been measured.

11. The portable electronic device of claim 10, wherein the program instructions further cause the portable electronic device to:
   measure an actual exposure time with the timer, the actual exposure time being the time between instructing a user to expose the diagnostic instrument to the biological sample and capturing the digital image of the diagnostic instrument; and
   record a corrected exposure time, wherein the corrected exposure time is based on a difference between the predetermined exposure time and the actual exposure time.

12. The portable electronic device of claim 11, wherein the program instructions further cause the portable electronic device to color correct the dominant camera-captured color of the at least one test medium based on the corrected exposure time.

13. The portable electronic device of claim 7, further comprising a data entry device, and wherein the program instructions further cause the portable electronic device to:
   receive patient information from the data entry device; and
   compare the test result with the patient information to determine a possible patient condition.

14. A method of performing a diagnostic test on a biological sample using a diagnostic device, the method comprising:
   exposing at least a portion of a test strip to the biological sample, wherein the test strip includes a plurality of reference-color indicators and a plurality of test pads, wherein each test pad of the plurality of test pads includes a reagent configured to change color in the presence of a different analyte in the biological sample; and
   receiving, at a processor of the diagnostic device, a digital image of at least a portion of the test strip after the exposing, wherein the portion includes at least a first reference-color indicator of the plurality of reference-color indicators and a first test pad of the plurality of test pads;
   determining, using the processor, a camera-captured color of the first test pad and a camera-captured color of the first reference-color indicator;
   estimating lighting conditions under which the digital image was acquired;
   determining, using the processor, a corrected color of the first test pad based at least on the camera-captured color of the first test pad and a color correction factor, wherein the color correction factor is derived at least in part from the camera-captured color of the first reference-color indicator; and
   determining, using the processor, a test result by comparing the corrected color of the first test pad to a set of test pad colors at the estimated lighting conditions under which the digital image was acquired.

15. The method of claim 14, wherein determining the test result includes determining a concentration of an analyte in the biological sample.

16. The method of claim 14, wherein estimating lighting conditions include estimating the lighting conditions based on at least one of luminance and irradiance.

17. The method of claim 14, further including displaying the determined test result on a display device.

18. The method of claim 14, further including displaying user instructions on a display device, wherein the user instructions are directions related to at least one of how to expose the test strip to the biological sample or how to acquire the digital image of the test strip.

* * * * *